United States Patent [19]

Tamuri et al.

[11] 4,284,722

[45] Aug. 18, 1981

[54] HEAT AND ACID-STABLE ALPHA-AMYLASE ENZYMES AND PROCESSES FOR PRODUCING THE SAME

[75] Inventors: Masaki Tamuri, Yokosuka; Mitsuo Kanno, Miyoshi; Yoshiko Ishii, Tokyo, all of Japan

[73] Assignee: CPC International Inc., Englewood Cliffs, N.J.

[21] Appl. No.: 93,407

[22] Filed: Nov. 13, 1979

Related U.S. Application Data

[63] Continuation-in-part of Ser. No. 934,135, Aug. 16, 1978, abandoned, which is a continuation of Ser. No. 764,923, Feb. 2, 1977, abandoned, which is a continuation-in-part of Ser. No. 678,513, Apr. 19, 1976, abandoned.

[51] Int. Cl.$^3$ .................. C12N 9/28; C12P 19/14; C12P 19/24; C12P 19/20
[52] U.S. Cl. ........................... 435/94; 435/96; 435/99; 435/202; 435/832; 426/48
[58] Field of Search ............... 435/99, 202, 814, 815, 435/832, 816, 172, 94, 96; 426/48

[56] References Cited

U.S. PATENT DOCUMENTS

| | | | |
|---|---|---|---|
| 3,031,380 | 4/1962 | Minagawa et al. | 435/172 |
| 3,720,583 | 3/1973 | Fisher | 435/96 |
| 3,808,102 | 4/1974 | Douros et al. | 435/202 |
| 3,922,200 | 11/1975 | Walon et al. | 435/96 |

FOREIGN PATENT DOCUMENTS 1285173  8/1972 United Kingdom.
1296839 11/1972 United Kingdom.

OTHER PUBLICATIONS

Campbell, "Purfication and Properties of an α-Amylase from Faculative Thermophilic Bacteria", *Arch. Biochem. Biophgsies,* vol. 54 (1955) pp. 154–161.
Yutani, et al., "Thermostrability of α-Amylase Produced from Thermophilic Bacteria", *Chem. Abst.,* vol. 83, No. 1 (1975) p. 290 Abs. No. 3107g.
Loginoua, "Enzymes of Thermophilic microorganisms, Exoenzymes, Amylase, *Chem. Abst.,* vol. 80, No. 25 (1974) p. 113 Abs. No. 142154d.
Motoe, et al., "Heat Resistant Amylase and Prostease from Thermophilic Fungi", *Chem. Abst.,* vol. 75, No. 26 (1971) p. 208, Abs. No. 150350b.

*Primary Examiner*—Thomas G. Wiseman

[57] ABSTRACT

Heat and acid-stable alpha-amylase enzymes having the following characteristics: (1) capable of retaining at least about 70% of their initial activity when held at 90° C. and at a pH of 6.0 for 10 minutes in the absence of calcium ion; (2) capable of retaining at least about 50% of their initial activity when held at 90° C. at a pH of 6.0 for 60 minutes in the absence of added calcium ion; and/or (3) capable of retaining at least about 50% of their initial activity at a temperature of 80° C. and at a pH of 4.5 in the presence of 5 mM calcium ion for 10 minutes. The preferred alpha-amylases are prepared by culturing a strain of a *Bacillus stearothermophilus* microorganism in a suitable culture medium. The novel alpha-amylases are useful in hydrolyzing and/or liquefying starch and due to their stability at low pH values they can be used in conjunction with other acid stable amylases such as gluco-amylase in either a soluble or an immobilized form.

18 Claims, 12 Drawing Figures

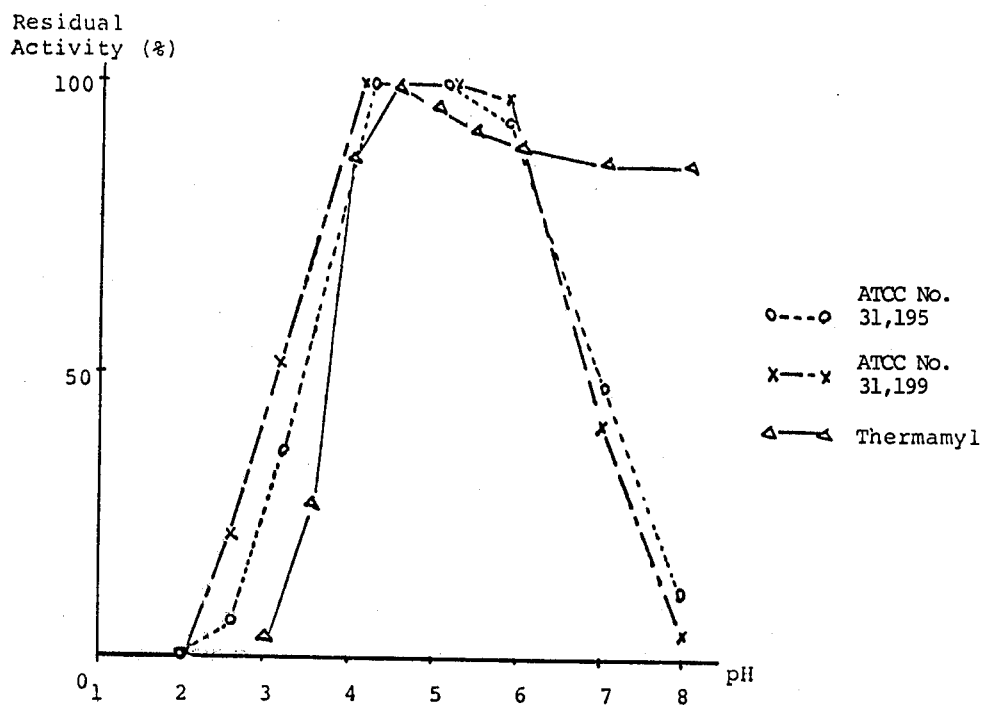
FIG. 1 Optimum pH
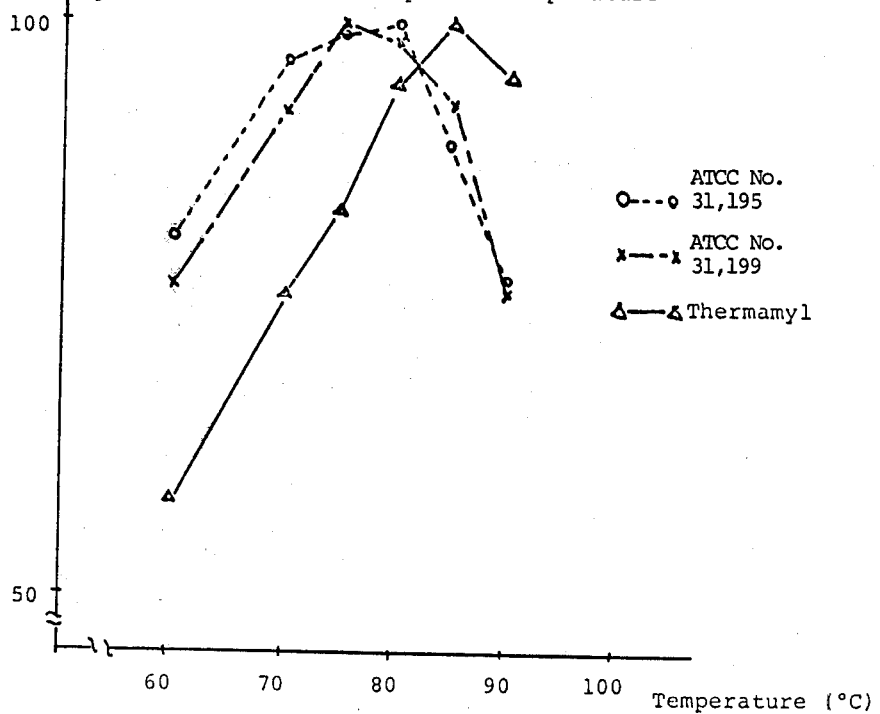
FIG. 2 Optimum Temperature

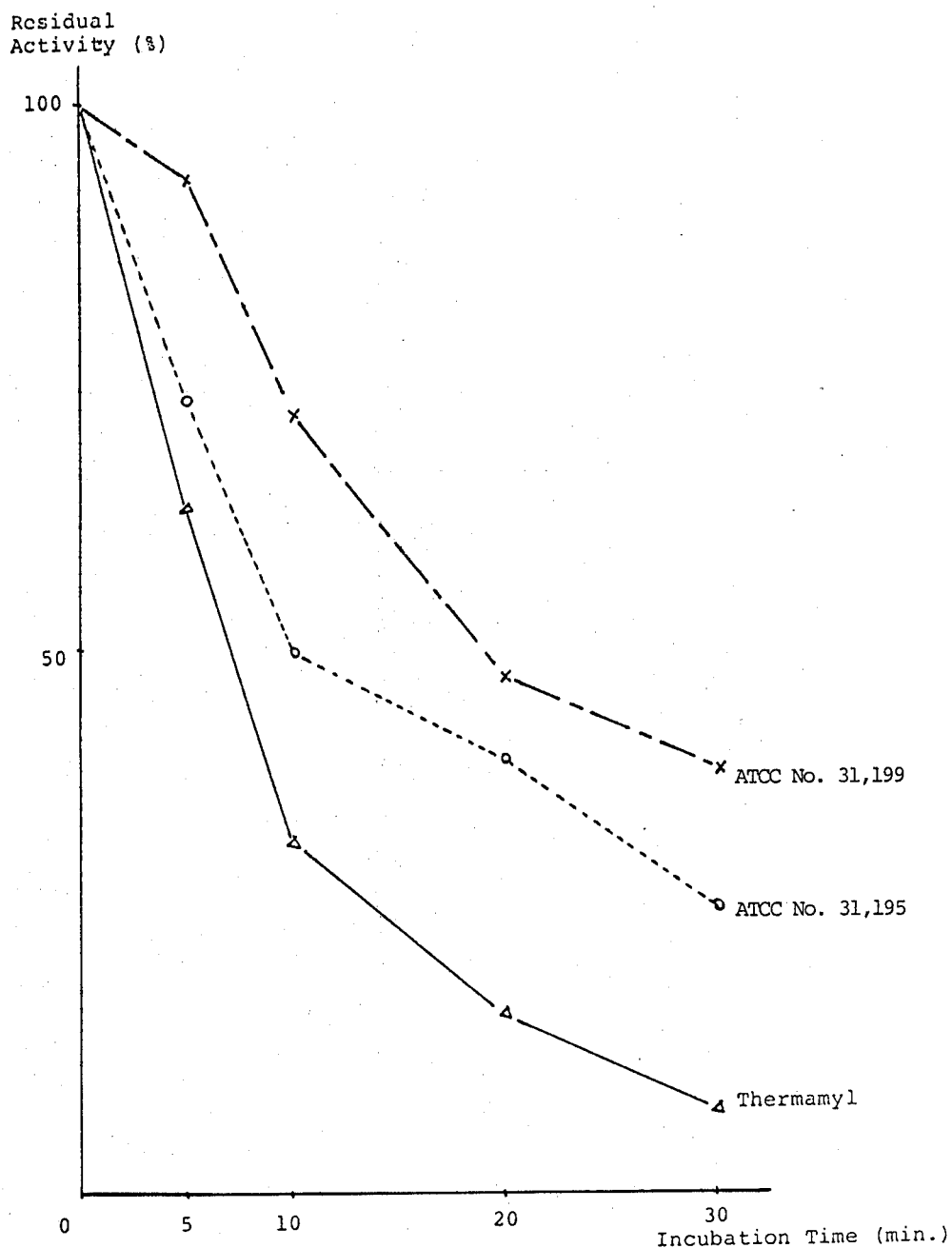

Thermo-Stability of α-Amylase at 90°C and pH 6.0

Thermostability of α-Amylase at 85°C and pH 4.55 in the Presence of 22.5% Starch Determination of Molecular Weight by SDS DISC Electrophoresis

FIG. II

HEAT AND ACID-STABLE ALPHA-AMYLASE ENZYMES AND PROCESSES FOR PRODUCING THE SAME

This application is a continuation-in-part of application Ser. No. 934,135, filed Aug. 16, 1978 abandoned which in turn is a continuation of application Ser. No. 764,923, filed Feb. 2, 1977, now abandoned, which in turn was a continuation-in-part of application Ser. No. 678,513, filed Apr. 19, 1976, now abandoned.

BACKGROUND OF THE INVENTION

1. Field of the Invention

This invention relates to novel heat and acid-stable alpha-amylase enzymes and processes for producing the same. This invention is also concerned with processes for using these novel alpha-amylase enzymes for hydrolyzing, liquefying and/or converting starch containing materials into starch hydrolysates.

2. Description of the Prior Art

Alpha-amylase enzyme preparations have been used to hydrolyze, liquefy and/or convert starch containing materials into starch hydrolysates as well as being used in detergent formulations. When alpha-amylase enzymes are used to treat starch containing materials, they are used as the initial step in the production of a number of starch hydrolysate materials, such as malto-dextrins, corn syrups, dextrose, levulose, maltose and others. The alpha-amylase enzyme hydrolyzes starch molecules to break them down into a variety of intermediate molecular weight fragments known as malto-dextrins. The malto-dextrins are subsequently treated with one or more additional enzyme preparations including glucoamylase, beta-amylase and glucose isomerase in order to produce the desired final product. Alternatively, a plurality of these enzyme preparations can be introduced into a slurry of the starch material simultaneously to directly produce the desired starch hydrolysate.

Alpha-amylase enzymes are available from a wide variety of sources. Most alpha-amylase enzymes are produced from bacterial sources such as *Bacillus subtilis, Bacillus licheniformis, Bacillus stearothermophilus* and others which are cultivated in an appropriate culture medium, the cells produced therefrom are then destroyed and the enzyme preparation is thereafter separated from the broth and purified.

Many of the commercially available alpha-amylase enzymes produced today are derived from *Bacillus subtilis* microorganisms. When these enzymes are used to convert starch to starch hydrolysates, they will generally have an optimal temperature ranging from about 80° to about 85° C., and an optimal pH of about 6.0. The conditions of temperature and pH necessary for efficient use of the enzyme have two disadvantages. Firstly, if starch is converted with the enzyme at a pH of about 6 and at a temperature of about 80° to about 85° C., a part of the reducing end-groups of the starch is isomerized, and in the subsequent conversion process, maltulose is produced which reduces the degree of recovery of the desired product, e.g., dextrose, levulose, or maltose. Secondly, the optimum pH of glucoamylase used in the conversion and saccharification process is generally about 4.5 in the case of *Aspergillus niger*-type enzymes and a pH of about 5.0 in the case of Rhizopus-type enzymes. Therefore, upon completion of the liquefaction step using the alpha-amylase enzyme, it has been necessary to adjust the pH from about 6 to 4.5 or 5.0. This pH adjustment increases the ion concentration and as a result, increases the load and consequent refining expense using the ion exchange resins used in the purification of the final product.

In recent years, various heat-stable alpha-amylase enzymes have been developed. Examples of such heat-stable alpha-amylase enzymes include those produced from microorganisms derived from *Bacillus stearothermophilis* as described by Ogasawara et. al., *J. Biochem.,* 67, 65, 77, and 83 (1970); G. B. Manning and L. L. Campbell, *J. Biol. Chem.,* 236, 2952, 2958 and 2962 (1961); S. L. Pfueller and W. H. Elliot, *J. Biol. Chem.,* 244, 48 (1969). More recently, alpha-amylase enzymes having good heat-stability in neutral or weakly alkaline solutions have been made available. These heat and alkaline stable alpha-amylase enzymes have been marketed under the brand name "Thermamyl". They are produced by cultivating microorganisms of the species *Bacillus licheniformis* as described in British patent specification No. 1,296,839, published Nov. 22, 1972, Madsen et. al., Die Stärke, 25, 304, 305 and 308 (1973) and Shigemasa Saito, ABB, 155, 290 (1973). While the alpha-amylase enzymes produced from *Bacillus licheniformis* have relatively good heat-stability in neutral and weakly alkaline solutions, they do not have suitable stability under acidic conditions to make their use economical from a commercial standpoint.

Accordingly, it is a principal object of the present invention to produce alpha-amylase enzymes which have good heat-stability as well as good stability under acidic conditions, particularly at pH values to render their use under conditions compatible with other amylases such as glucoamylase.

SUMMARY OF THE INVENTION

The present invention is directed to novel heat and acid-stable alpha-amylase enzymes which are characterized as (1) capable of retaining at least about 70% of their initial alpha-amylase activity when held at 90° C. and at a pH of 6.0 for 10 minutes in the absence of added calcium ion; (2) capable of retaining at least about 50% of their initial alpha-amylase activity when held at 90° C., at a pH of 6.0 for 60 minutes in the absence of added calcium ion and (3) capable of retaining at least about 50% of their initial alpha-amylase activity at a temperature of 80° C. and at a pH of 4.5 in the presence of 5 mM of calcium ion for 10 minutes. The enzymes of the invention are also capable of retaining at least about 50% of their initial activity at a temperature of 85° C. and at a pH of 4.55 for 30 minutes in the presence of 5 mM of calcium ion and 22.5%, by weight starch, d.s. These enzymes are preferably derived from a Bacillus microorganism and more preferably a *Bacillus stearothermophilus* microorganism.

The alpha-amylase enzymes of the present invention have a molecular weight of at least about 90,000 as determined by sodium dodecyl sulfate (hereinafter "SDS") disc electrophoresis and they are characterized as being substantially free of protease activity, e.g., they generally have a protease/alpha-amylase ratio of less than 3, and preferably less than 1.

The novel alpha-amylase enzymes of the present invention are produced by cultivating in a suitable medium a *Bacillus stearothermophilus* microorganism, preferably culturing a strain selected from the group consisting of *Bacillus stearothermophilus* ATCC Nos. 31,195, 31,196, 31,197, 31,198, 31,199, variants, mutants and sub-mutants thereof and thereafter recovering the alpha-amylase enzyme produced.

BRIEF DESCRIPTION OF THE DRAWINGS

FIG. 1 illustrates the relationship of the optimal pH of two of the enzymes of the invention with Thermamyl alpha-amylase.

FIG. 2 illustrates the relationship of the optimal temperature of two of the enzymes of the invention with Thermamyl-alpha-amylase.

FIG. 3 illustrates the relationship of the thermostability of two of the enzymes of the invention with Thermamyl alpha-amylase at 80° C., pH 4.5 with 5 mM of $Ca^{++}$.

DESCRIPTION OF THE PREFERRED EMBODIMENTS

Figure 4:
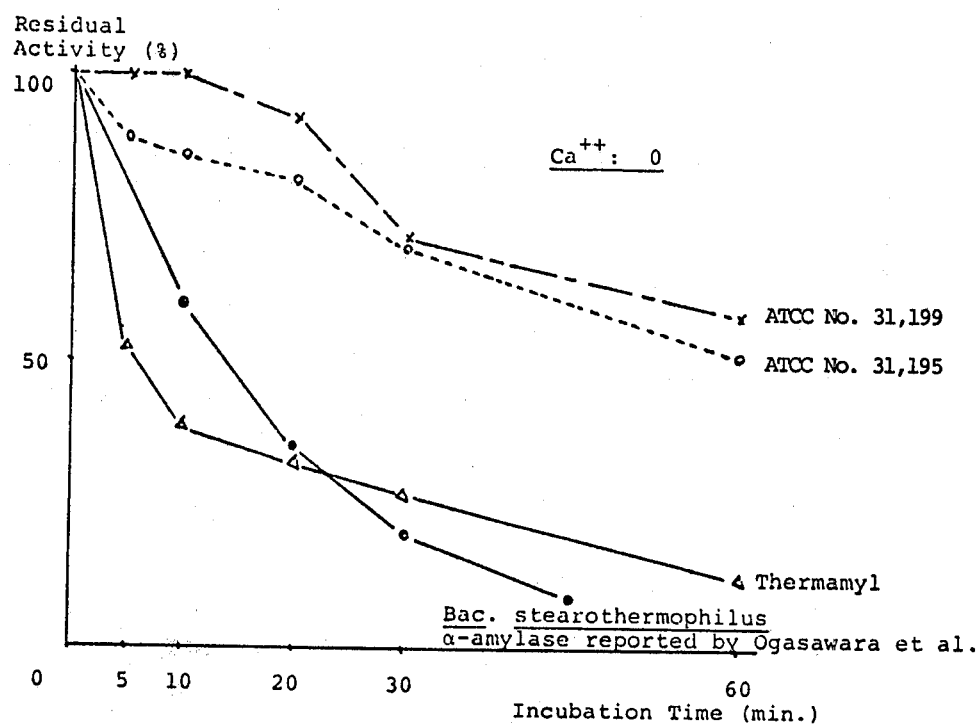
FIG. 4 illustrates the relationship of the thermostability of two of the enzymes of the present invention with Thermamyl alpha-amylase at 90° C. and at a pH of 6.0.

The production and thermal stability of alpha-amylase from various kinds of microorganisms were screened under various conditions such as growth temperature (37° C., 45° C., 55° C., and 70° C.), pH (5.0 and 7.0) and media. It was found that thermophilic ray fungi isolated at 55° C. and thermophilic fungi at 45° C. produce thermolabile alpha-amylase in high yields, whereas thermophilic bacteria at 70° C. produce thermostable alpha-amylase in low yields. Based upon these initial studies the screening of the microorganisms for acid- and thermostability of alpha-amylase was conducted by culturing at 55° C. and 70° C.

A total of 550 samples of microbial sources including soil, hot-spring water, compost, etc. were collected from various locations.

The acid- and thermostabilities were determined by assaying alpha-amylase activity before and after heat treatment of culture filtrates at 80° C. and pH 5.0 for 10 minutes in the presence of 10 mM calcium ion.

The alpha-amylase activity was determined as follows:

0.2% by weight (All percentages in this specification are by weight unless otherwise indicated.) soluble starch solution was prepared weekly as follows: 200 mg soluble starch in approximately 50 ml of 0.2 M acetate buffer (pH 4.5) containing 0.013 M $CaCl_2.2H_2O$ was heated to 100° C. in boiling water, and the resultant solution was made to 100 ml with the same buffer. A test tube containing 0.1 ml of enzyme solution and 0.3 ml of 0.2% soluble starch solution was incubated for 5 minutes at 60° C. The reaction was stopped by adding 1.0 ml of 0.5 N acetic acid. After 3.0 ml of 0.015% iodine solution was added and stirred, the optical density was read at 700 millimicrons against $H_2O$. A test tube without enzyme served as a blank and its optical density at 700 millimicrons was designated as $OD_b$. One unit of enzyme was that amount which catalyzes a 10% decrease in blue value per minute under the conditions described above.

$$NML \text{ units} = \frac{(OD_b - OD) \times 100}{OD_b \times 5 \times 10}$$

Except where indicated to the contrary, the alpha-amylase activity reported was determined by the above procedure (NML units). Where the alpha-amylase activity is designated as CPC alpha-amylase units, the CPC units are approximately 1/140 of the NML units.

The CPC alpha-amylase units of activity are determined by the following procedure:

One milliliter of properly diluted enzyme solution is added to 10 milliliters of a 1% soluble starch—0.03 M acetic acid buffer solution (pH 6.0) and the reaction is carried out for 10 minutes at 60° C. One milliliter of the reaction solution is put in a 100 ml graduated flask containing 50 ml of 0.02 N hydrochloric acid, and after adding 3 milliliters of 0.05% iodine solution thereto, the total volume is made up to 100 ml by the addition of water. The blue color which develops is measured for absorbance at 620 millimicrons. The amount of the enzyme required to decompose 10 mg of starch in one minute is defined as 1 CPC unit.

$$1 \text{ } CPC \text{ unit} = \frac{D_o - D_s}{D_o} \times \frac{50}{10 \times 10} \times \text{(dilution factor)}$$

where, $D_o$ = absorbance of control solution (water is added instead of the enzyme solution)

$D_s$ = absorbance of the reaction solution

The culturing conditions and media used in the screening study are summarized in Table 1.

The results of the first and second screening studies are reported in Table 2.

TABLE 1

| Culturing Conditions and Media | | | |
|---|---|---|---|
| Conditions | Plate Culture[1] | Slant Culture[2] | Flask Culture[3] |
| (a) | 55° C., pH 5 | 55° C., pH 5 | 50° C., pH 6 |
| (b) | 55° C., pH 7 | 55° C., pH 7 | 50° C., pH 7 |
| (c) | 70° C., pH 5 | 70° C., pH 5 | 60° C., pH 6 |

TABLE 1-continued

| Culturing Conditions and Media | | | | | |
|---|---|---|---|---|---|
| (d) | 70° C., pH 7 | | 70° C., pH 7 | | 60° C., pH 7 |
| ¹Medium for Plate Culture (B-B) | | | ²Medium for Slant Culture (B-D) | | ³Medium for Flask Culture (B-M) |
| Amylopectin | 0.02% | Soluble Starch | 1.0% | | 3.0% |
| (NH₄)₂HPO₄ | 0.025% | Bacto-tryptone (Difco) | 0.5% | | 0.5% |
| Yeast ext. | 0.025% | Yeast ext. | 0.5% | | 1.0% |
| Na-Citrate | 0.01% | CaCl₂ . 2H₂O | 0.05% | | 0.05% |
| MgSO₄ . 7H₂O | 0.05% | MnCl₂ . 4H₂O | 0.05% | | — |
| KCl | 0.15% | MgSO₄ . 7H₂O | — | | 0.05% |
| CaCl₂ . 2H₂O | 0.05% | KH₂PO₄ | 0.1% | | 0.1% |
| Agar | 2.0% | Agar | 2.0% | | — |

TABLE 2

Results of Screening

| 1st Screening | | | 2nd Screening Distribution of α-amylase producers | | | | |
|---|---|---|---|---|---|---|---|
| Isolation Conditions | Strains Isolated | RA* | 100~200 U/ml | ~500 U/ml | ~1,000 U/ml | ~2,000 U/ml | ~2,500 U/ml |
| 55° C., pH 5.0 | Ray fungi | — | 16 | 43 | 46 | 34 | 1 |
| | 503 strains | + | 0 | 0 | 0 | 0 | 0 |
| | Bacteria | — | 9 | 4 | 2 | 0 | 0 |
| | 292 strains | + | 0 | 1 | 2 | 0 | 0 |
| 55° C., pH 7.0 | Ray fungi | — | 16 | 50 | 34 | 27 | 5 |
| | 629 strains | + | 0 | 0 | 0 | 0 | 0 |
| | Bacteria | — | 5 | 3 | 2 | 0 | 0 |
| | 769 strains | + | 4 | 3 | 0 | 0 | 0 |
| 70° C., pH 5.0 | Bacteria | — | 0 | 1 | 0 | 0 | 0 |
| | 841 strains | + | 7 | 1 | 1 | 3 | 0 |
| 70° C., pH 7.0 | Bacteria | — | 0 | 0 | 0 | 0 | 0 |
| | 1,326 strains | + | 15 | 2 | 0 | 0 | 0 |

*RA: Remaining activity after heat treatment at 80° C. and pH 5.0 for 10 min. All RA positive strains showed about 100% of remaining activity.

About 25% of thermophilic ray fungi isolated at 55° C. showed 100–2,500 units of alpha-amylase production per milliliter of culture broth, but no activity remained after heat treatment (80° C., 10 minutes, pH 5.0).

A total of 35 strains from 1,061 thermophilic bacterial strains isolated at 55° C. showed 100–1,000 units of alpha-amylase production, and 10 of those strains produced a thermostable alpha-amylase. Almost all of the alpha-amylases from thermophilic bacteria isolated at 70° C. showed acid- and thermostability; and the highest producers were obtained from pH 5.0 isolates.

The relationship between activity and clear zone size in the last 219 strains isolated at 70° C. and pH 5.0 was examined. The results of this study are shown in Table 3 where it can be seen that 90% of these strains gave clear zone of less than 3 cm in diameter and produced 0–200 units of alpha-amylase. The highest production was obtained from strains which gave a clear zone of more than 3 cm in diameter, but these represented only 10% of the tested strains.

TABLE 3

Relationship between Activity and Clear Zone Size of Isolated Strain

| Activity in Flask (U/ml) | Clear Zone Size on Isolation Plate (cm in diameter) | | | | Total |
|---|---|---|---|---|---|
| | <2 | –3 | –4 | 4< | |
| 0–100 | 153 | 40 | 15 | 0 | 208 |
| –200 | 3 | 2 | 1 | 0 | 6 |
| –500 | 0 | 0 | 2 | 0 | 2 |
| –1,000 | 0 | 0 | 1 | 0 | 1 |
| –1,500 | 0 | 0 | 1 | 1 | 2 |
| Total | 156 | 42 | 20 | 1 | 219 |

Based on the above tests, it has been found that the isolation of bacterial colonies having a clear zone of more than 3 cm in diameter on the plate medium used in the tests at 70° C. and at a pH of 5.0 is an excellent method for screening for microorganisms capable of producing high yields of acid- and thermostable alpha-amylase enzymes.

As a result of this screening, five strains were selected as the highest producers of acid- and thermostable alpha-amylase enzyme producers.

Each of the five strains in purified form as described below have been deposited in the permanent collection of the American Type Culture Collection (ATCC), 12301 Parklawn Drive, Rockville, Md. 20852. ATCC is maintaining these strains pursuant to a contract between ATCC and CPC International Inc., the assignee of this patent application.

The contract between ATCC and CPC International Inc. provides for permanent availability of the cultures or sub-cultures to the public, without restriction upon (1) issuance of a United States patent describing and identifying the subject deposits and disclosing the ATCC numbers assigned thereto; or (2) publication or laying open to public inspection of any United States or foreign patent application describing and identifying the subject deposits and disclosing the ATCC numbers assigned thereto. CPC International Inc. has agreed that, if any of these cultures on deposit should die, or is destroyed, during the effective life of the patent, it will be replaced with a living culture of the same organism. In addition, CPC International Inc. has authorized ATCC to grant the U.S. Patent and Trademark Office and the West German Patent Office free access to the cultures or sub-cultures at any time upon request by an authorized official of such offices.

| Organisms Deposited | |
|---|---|
| NML Strain No. | ATCC No. |
| *Bacillus stearothermophilus* B-501 | 31,195 |
| *Bacillus stearothermophilus* B-634 | 31,196 |
| *Bacillus stearothermophilus* B-781 | 31,197 |
| *Bacillus stearothermophilus* B-905 | 31,198 |
| *Bacillus stearothermophilus* B-968 | 31,199 |

In addition, NML strains B-501 and B-781 have been deposited with the Fermentation Research Institute, Industrial Technology Agency, MITI, as FRI Nos. 3389 and 3390, respectively.

The bacteriological characteristics of the five (5) selected strains deposited at ATCC are as follows:

(1) Morphological Characteristics:
A. Shape and size of cells: 0.6×2-3 microns; individual rods seldom in chains (all strains)
B. Pleomorphicity: Negative (all strains)
C. Motility: Motile and have flagella (all strains)
D. Spore: 0.6×1.0-1.5 microns, ovular shaped; racket-shaped spore case (all strains)
E. Gram stain: Positive (all strains)
F. Acid fast: Negative (all strains)

(2) Growth on Various Media:
A. Nutrient agar plate: Active spreading colonies with coarse surface and rough edge (all strains)
B. Nutrient agar slant: Good growth, white opaque, active spreading, comb-like outgrowths (all strains)
C. Nutrient broth liquid culture: Transparent brown, white surface mat (all strains)
D. Nutrient gelatin stab culture: Liquefaction (all strains)
E. Nutrient gelatin agar plate: Wide clear zone (all strains)
F. Salt-nutrient liquid culture: Growth inhibition in 2% salt (all strains)
G. Milk agar plate: Celar zone formation by hydrolysis of casein (all strains)
H. Glucose agar slant: Good growth, similar colonies to those on nutrient agar (all strains)
I. Proteose peptone agar slant: No growth (all strains)

(3) Physiological Characteristics:
A. Nitrate reduction: Positive (all strains)
B. Catalase test: Positive (all strains)
C. Vogues-Proskauer reaction: Positive (all strains)
D. Utilization of citric acid: Positive (all strains)
E. Formation of hydrogen sulfide: Positive (all strains)
F. Formation of hydrogen sulfide: Positive (all strains)
G. Hydrolysis of starch: Strong hydrolysis (all strains)
H. Formation of acid and gas: Positive for acid but no gas formation from glucose xylose, arabinose, mannitol (all strains)
I. Temperature and pH for growth:

| | ATCC No. 31,195 (B-501) | ATCC No. 31,197 (B-781) |
|---|---|---|
| 37° C. | no growth | slight growth |
| 42° C. | slight growth | moderate growth |
| 50-70° C. | good growth | good growth |
| pH range for growth | 5-8 | 5-8 |
| Optimum pH | 6-7 | 6-7 |

The above tests were done in accordance with "Laboratory Methods in Microbiology" by W. F. Harrigan et. al., and the "Manual of Microbiological Methods" published by the American Bacteriological Association.

From the foregoing characteristics, the five (5) selected strains were identified as *Bacillus stearothermophilus* in accordance with Bergey's Manual of Determinative Bacteriology, the 8th Edition.

These five strains were further purified by the plates-treaking method. The results of the isolation, culturing and purification conditions with respect to the five selected strains are summarized in Table 4. As it can be seen from Table 4, the purified strain of ATCC No. 31,199 (B-968) was the best of the five selected strains, producing 2,111 NML units of alpha-amylase units of activity per milliliter of culture broth (about 15 CPC units).

TABLE 4

Summary of Selected Strains

| | 1st Screening Isolation Conditions | | | 2nd Screening | | | Purification | | |
|---|---|---|---|---|---|---|---|---|---|
| ATCC No. | Temp. (°C.) | pH | Source | Activity (U/ml) | Culture Time (hr) | Culture Conditions | Activity (U/ml) | Culture Time (hr) | Culture Conditions |
| 31,195 | 70 | 5.0 | Farm soil | 1,152 | 89 | 60° C., pH 6 | 1,372 | 72 | 60° C., pH 6 |
| 31,196 | 55 | 5.0 | Soil from starch-settling basin | 700 | 112 | 50° C., pH 6 | 687 | 65 | 50° C., pH 6 |
| 31,197 | 70 | 5.0 | Soil from hot-spring | 591 | 42 | 60° C., pH 6 | 1,002 | 26 | 60° C., pH 6 |
| 31,198 | 70 | 5.0 | Fermented oats in silo | 1,217 | 41 | 60° C., pH 6 | 859 | 65 | 60° C., pH 6 |
| 31,199 | 70 | 5.0 | Compost | 1,098 | 40 | 60° C., pH 6 | 2,111 | 42 | 55° C., pH 6 |

In the production of the alpha-amylase enzymes of the present invention a strain of a microorganism capable of producing an acid- and heat-stable alpha-amylase enzyme such as one which meets the tests in Table 3 (e.g., *Bacillus stearothermophilus* strains ATCC Nos. 31,195, 31,196, 31,197, 31,198 or 31,199) is cultivated in a nutrient medium known for cultivating thermophilic bacteria. Such culture mediums should contain an assimilable carbon and nitrogen source together with other essential nutrients.

Suitable assimilable carbon sources include carbohydrates such as starches, hydrolyzed starches, corn meal, wheat flour, etc. The carbohydrate concentration to be used in the medium may vary widely, e.g., it may range from about 1% w/v to about 25% w/v, and preferable ranging from about 10% w/v to about 20% w/v, the percentages being calculated as dextrose. The preferred assimilable carbohydrate is starch or partially hydrolyzed starch (and when used on a weight basis they are present in an amount ranging from 1 to 5%, by weight).

The nitrogen source in the nutrient medium may be of inorganic and/or organic nature. Suitable inorganic nitrogen sources include ammonium salts, and inorganic nitrates, etc. Suitable organic nitrogen sources include peptone, meat extract, yeast extract, casein, corn steep liquor, malt extract, soybean flour, skim milk, etc.

In addition, the nutrient medium should contain the usual trace substances such as the inorganic salts which include calcium chloride, magnesium sulfate, phosphates, sodium chloride, potassium chloride, etc.

These carbon sources, nitrogen sources and inorganic salts can be used singly or in appropriate combinations. In addition, a small quantity of metallic salts, vitamins, amino acids, etc. can be used to promote the growth and productivity of the bacteria.

The culturing conditions used to produce the alpha-amylase enzymes of the present invention are the same as normally used in the cultivation of thermophilic bacteria. Preferably, the strain is cultivated in a deep liquid culture medium under agitation and aeration for 1 to 5 days at 50° C. to 70° C. at a pH of 5 to 9. The enzyme accumulates in the cultured medium.

Following the production of the alpha-amylase enzyme of the present invention, the microbial cells are then removed by conventional means such as centrifugation. The filtrate is then preferably subjected to salting out by the addition of inorganic salts such as ammonium sulfate, sodium sulfate or magnesium sulfate, and/or by use of water miscible organic solvents such as acetone, ethanol, 2-propanol, etc. to precipitate out the enzyme so that it can be concentrated. It is also possible to recover the alpha-amylase by adding starch to the filtrate so that the alpha-amylase will sorb to the starch.

A preferred means for purifying the enzyme from the filtrate containing the enzyme includes the steps of treating the filtrate with cold acetone in twice the volume of the filtrate to precipitate the enzyme. The precipitated enzyme is then dissolved in a 0.05 M tris-hydrochloric acid buffer solution (pH 8.5) and it is then passed through a DEAE-cellulose column which is equilibrated with the same buffer solution. At a pH of 8.5 the non-alpha-amylase proteins, pigments, etc. are adsorbed to the DEAE-cellulose whereas most of the alpha-amylase remains in solution. The filtrate containing the alpha-amylase enzyme is referred to herein as the "partially refined enzyme". The partially refined enzyme can be further refined by dialysis against a 0.01 M tris-hydrochloric acid buffer solution (pH 7.0) and then passed through a hyrdoxylapatite column which is equilibrated with the same buffer solution. The enzyme sorbs to the column in this step. The sorbed enzyme is eluted out by linearly increasing the ammonium sulfate concentration from 0 to 0.5 M.

The partially refined enzyme thus obtained is, after being concentrated, passed through a Sephadex G-150 column. The enzyme is weakly adsorbed to the Sephadex and it is eluted out in the fraction of below 10,000 molecular weight. The activity of the refined enzyme obtained in this way is increased by 100 times over the original filtrate, but in disc electrophoresis, bands of a few other proteins are also observed besides that of the alpha-amylase enzyme—and crystallization of the enzyme has not yet been accomplished.

The following examples serve to more fully describe the manner of making and using the above-described invention, as well as to set forth the best modes contemplated for carrying out various aspects of the invention.

It is to be understood that these examples in no way serve to limit the true scope of this invention, but rather, are presented for illustrative purposes only. It will be understood that all proportions are in parts by weight, unless otherwise indicated.

EXAMPLE 1

A culture medium containing 3.0% (by weight) soluble starch, 0.5% bactotryptone, 1.0% yeast extract, 0.05% calcium chloride, 0.05% magnesium sulfate, and 0.1% potassium dinydrogen phosphate was adjusted to pH 7.0. A 50 ml aliquot of this medium was poured into a 500 ml conical flask and sterilized for 15 minutes at 121° C. The sterilized medium was inoculated with ATCC No. 31,195 (B-501) strain of *Bacillus stearothermophilus* and cultured under agitation for 4 days at 60° C. After the cultivation, the microbial cells were removed by centrifugation. The enzymatic activity of the filtrate per one milliliter was 10 CPC alpha-amylase units (determined by CPC method described above). To this filtrate, two volumes of acetone were added to precipitate the enzyme which was subsequently dissolved in a 0.05 M Tris-HCl buffer (pH 8.5). Then the solution was passed through a DEAE-cellulose column which had been equilibrated with the same buffer solution. The alpha-amylase enzyme was not sorbed to the DEAE-cellulose while most other proteins, pigments, etc., were sorbed to the DEAE-cellulose were thus removed. The partially refined enzyme thus obtained was first concentrated and then passed through a Sephadex G-150 column. The enzyme was weakly sorbed to the Sephadex and it was eluted out in the fraction of below 10,000 molecular weight. The refined enzyme thus obtained was made into a powdered, refined enzyme by freeze-drying and its relative activity was about 200 CPC units/mg of protein.

EXAMPLE 2

A culture medium which contained 3% corn starch, 0.5% peptone, 1% corn steep liquor, 0.05% calcium chloride, 0.05% manganese chloride, 0.05% magnesium chloride, and 0.05% potassium chloride was adjusted to pH 7.5. A 50 ml aliquot of this culture medium was placed in a 500 ml conical flask and sterilized for 15 minutes at 121° C. The sterilized medium was inoculated with ATCC No. 31,196 (B-781) strain of *Bacillus stearothermophilus* and agitated for 4 days at 55° C. After the cultivation, the microbial cells were removed by centrifugation. The alpha-amylase activity in the filtrate was 14 CPC units/ml. The alpha-amylase was precipitated by the addition of twice the volume of filtrate of 2-propanol. The precipitate was formed into a dry powder by freeze-drying. The activity of the crude enzyme powder was 3 CPC units/mg. A refined, powdered enzyme having an activity of 230 units/mg was obtained from this crude enzyme powder by refining by the procedure of Example 1.

The five isolated and selected strains (i.e., ATCC Nos. 31,195, 31,196, 31,197, 31,198 and 31,199) were tested to determine the effect of temperature and pH on alpha-amylase production. The alpha-amylase activity in the experiments was expressed as the mean value of the peak activity of triplicate flasks. The medium composition used for both the pre-culture and main-culture is the same shown in Table 1 (a B-M medium). The results of these experiments are summarized in Table 5.

TABLE 5
Effect of Temperature and pH on α-Amylase Production

| ATCC No. | Temp. (°C.) | pH 5.5 | pH 6.0 | pH 6.5 | pH 7.0 | pH 7.5 | pH 8.0 |
|---|---|---|---|---|---|---|---|
| 31,195 | 50 | | 1,055 (90) | | 514 (90) | | 100 (90) |
| | 55 | | 1,355 (90) | | 1,334 (90) | | 120 (90) |
| | 60 | | 942 (48) | | 1,490 (90) | | 1,040 (90) |
| | 65 | | 0 (90) | | 100 (90) | | 30 (90) |
| 31,196 | 45 | | 418 (89) | | 368 (89) | | |
| | 50 | | 477 (65) | | 681 (41) | | |
| | 55 | | 608 (41) | | 916 (41) | | |
| | 60 | | 932 (68) | | 975 (68) | 1,168 (43) | 1,051 (43) |
| | 65 | | 403 (43) | | 356 (20) | 262 (20) | 191 (68) |
| | 70 | | 24 (43) | | 224 (20) | 155 (20) | 59 (43) |
| 31,197 | 50 | | 751 (44) | 720 (44) | 679 (44) | 1,001 (44) | |
| | 55 | | 1,057 (44) | 1,155 (27) | 1,012 (44) | 1,330 (27) | |
| | 60 | | 1,085 (44) | 1,166 (27) | 1,084 (27) | 1,139 (27) | |
| | 65 | | 1,687 (44) | 615 (27) | 815 (27) | 848 (27) | |
| 31,198 | 50 | | 184 (68) | 272 (68) | 480 (68) | 352 (68) | 152 (68) |
| | 55 | | 768 (44) | 752 (68) | 832 (44) | 880 (44) | 955 (44) |
| | 60 | | 621 (44) | 675 (44) | 739 (44) | 1,104 (44) | 1,123 (44) |
| | 65 | | 1,340 (68) | 782 (44) | 776 (44) | 689 (44) | 661 (44) |
| 31,199 | 45 | 143 (139) | 133 (139) | 113 (139) | 115 (139) | 86 (139) | |
| | 50 | 686 (139) | 663 (139) | 543 (139) | 493 (139) | 491 (139) | |
| | 55 | 1,608 (43) | 1,365 (43) | 1,267 (43) | 1,025 (43) | 946 (43) | |
| | 60 | 1,485 (43) | 1,457 (43) | 1,295 (43) | 1,154 (43) | 1,117 (43) | |
| | 65 | | 0 (65) | 0 (65) | 0 (65) | 0 (65) | 0 (65) |

It can be seen from Table 5 that the optimum conditions for ATCC Nos. 31,195 and 31,196 were 60° C., pH 7.0 and 60° C., pH 7.5, respectively. ATCC Nos. 31,197 and 31,198 produced considerable amounts of alpha-amylase when cultured at 65° C., but this high temperature cultivation was not suitable for producing good alpha-amylase activity for the other isolated strains. At 55° C. to 60° C., the optimum medium pH was found to be 8.0 for alpha-amylase production for strain ATCC No. 31,198, and the optimum medium pH for strain ATCC No. 31,199 was 5.5.

Tables 6 and 7, respectively, (1) summarize the alpha-amylase production of the five isolated strains using repeatedly transferred slants (each strain was repeatedly transferred 9–11 times on two kinds of slant media, and then liquid-cultured to find a suitable slant medium capable of maintaining stable production of alpha-amylase) and (2) determine the effect of medium volume on alpha-amylase production (the medium volume in 500 ml flasks was changed to examine the aeration effect on the production of alpha-amylase by each strain.

TABLE 6
α-Amylase Production Using Repeatedly Transferred Slants

| ATCC No. | Media and Number of Transfers | | Flask Culture Activity, U/ml (Culture time, HR) | Conditions Temp. (°C.) | pH |
|---|---|---|---|---|---|
| 31,195 | BD*1, | 1 | 856 (90) | 60 | 7.0 |
| | BD, | 10 | 910 (43) | " | " |
| — | NA*2, | 10 | 140 (72) | " | " |
| 31,196 | BD, | 2 | 976 (26) | 60 | 7.5 |
| | BD, | 10 | 1,503 (26) | " | " |
| | NA, | 10 | 1,550 (26) | " | " |
| 31,197 | BD, | 1 | 1,330 (27) | 55 | 7.5 |
| | BD, | 10 | 1,127 (26) | " | " |
| | NA, | 10 | 1,420 (26) | " | " |
| 31,198 | BD, | 4 | 736 (44) | 60 | 8.0 |
| | BD, | 11 | 712 (44) | " | " |
| | NA, | 11 | 1,117 (44) | " | " |
| 31,199 | BD, | 2 | 1,163 (44) | 55 | 5.5 |
| | BD, | 9 | 1,013 (68) | " | " |
| | NA, | 9 | 775 (68) | " | " |

*1 Slant medium for screening
*2 Nutrient Agar Slant

TABLE 6-continued
α-Amylase Production Using Repeatedly Transferred Slants

| Soluble starch | 1.0% | Bacto-peptone (Difco) | 0.5% |
|---|---|---|---|
| Bacto-tryptone (Difco) | 0.5% | Bacto-beef ext. (Difco) | |
| Yeast ext. | 0.5% | | 0.3% |
| CaCl$_2$ . 2H$_2$O | 0.05% | Agar | 2.0% |
| MnCl$_2$ 4H$_2$O | 0.05% | pH | 7.2 |
| KH$_2$PO$_4$ | 0.1% | | |
| Agar | 2.0% | | |
| pH | 5.0 | | |

TABLE 7
Effect of Medium Volume on Amylase Production

| ATCC No. | Number of slant-transfers | Conditions Temp. (°C.) | pH | Flask Culture Med. volume ml/500 ml flask | Activity, U/ml (culture time, hr) |
|---|---|---|---|---|---|
| 31,195 | BD-11 | 60 | 7.0 | 30 | 150 (65) |
| | | | | 40 | 127 (65) |
| | | | | 50 | 1,192 (41) |
| | | | | 60 | 790 (41) |
| | | | | 70 | 146 (65) |
| 31,196 | BD-2 | 60 | 7.5 | 30 | 954 (26) |
| | | | | 40 | 966 (26) |
| | | | | 50 | 976 (26) |
| | | | | 60 | 1,236 (26) |
| | | | | 70 | 651 (43) |
| 31,197 | BD-3 | 55 | 7.5 | 30 | 1,435 (41) |
| | | | | 40 | 1,590 (41) |
| | | | | 50 | 1,510 (41) |
| | | | | 60 | 1,380 (41) |
| | | | | 70 | 840 (41) |
| 31,198 | BD-4 | 60 | 8.0 | 30 | 689 (44) |
| | | | | 40 | 651 (44) |
| | | | | 50 | 736 (44) |
| | | | | 60 | 939 (44) |
| | | | | 70 | 777 (44) |
| 31,199 | BD-2 | 55 | 5.5 | 30 | 1,131 (44) |
| | | | | 40 | 1,240 (44) |
| | | | | 50 | 1,163 (44) |
| | | | | 60 | 1,054 (68) |

TABLE 7-continued

Effect of Medium Volume on Amylase Production

| ATCC No. | Number of slant-transfers | Flask Culture Conditions Temp. (°C.) | pH | Med. volume ml/500 ml flask | Activity, U/ml (culture time, hr) |
|---|---|---|---|---|---|
| | | | | 70 | 1,224 (68) |

Two strains of the present invention (ATCC Nos. 31,195 and 31,199) were purified and the alpha-amylase properties produced therefrom were compared with purified Thermamyl Liquid 60, Batch AN 1005 by the procedure described below.

Alpha-amylase enzyme was precipitated from the culture filtrates of ATCC Nos. 31,195 and 31,199 or from Thermamyl alpha-amylase (twice diluted) by adding two volumes of cold acetone. The precipitate was collected by centrifugation and dissolved in 0.025 M calcium acetate solution. Soluble starch was added to the solution so as to make a 20% starch suspension. This suspension was heated at 85° C. for 30 minutes and the precipitate was removed by centrifugation. Then, the solution was dialyzed against 0.05 M Tris-HCl buffer (pH 8.5) containing 10 mM $Ca^{++}$, replacing the buffer twice. The dialyzate was applied to a DEAE-cellulose column which had been equilibrated with the dialysis buffer. The alpha-amylase was not adsorbed by the column and eluted with the same buffer. The fractions having alpha-amylase activity were collected and the alpha-amylase enzyme was concentrated by acetone precipitation. The alpha-amylase activity was determined by the CPC method described above. The purification process is summarized in Table 8.

TABLE 8

Purification of α-Amylase

| Purification Process | Culture Broth or Crude Enzyme Preparation | Acetone Precipitation | Heat-Treatment | DEAE-Cellulose |
|---|---|---|---|---|
| α-Amylase | | | | |
| ATCC No. 31,195 | | | | |
| Total Activity (CPC Units) | 9,870 | 8,640 | 8,420 | 2,400 |
| Total Protein (mg) | 7,990 | 2,016 | 1,450 | 15.7 |
| Specific Activity (Units/mg) | 1.2 | 4.3 | 5.8 | 152.9 |
| Yield (%) | 100 | 87.5 | 85.3 | 24.3 |
| ATCC No. 31,199 | | | | |
| Total Activity (CPC units) | 9,910 | 8,210 | 7,214 | 2,310 |
| Total Protein (mg) | 4914 | 1969 | 1206 | 33 |
| Specific Activity (Units/mg) | 2.0 | 4.2 | 6.0 | 70 |
| Yield (%) | 100 | 82.8 | 72.8 | 23.3 |
| Thermamyl | | | | |
| Total Activity (CPC units) | 12,100 | 9,400 | 9,540 | 2,410 |
| Total Protein (mg) | 684 | 286 | 183 | 24 |
| Specific Activity (units/mg) | 17.7 | 32.9 | 52.1 | 100.4 |
| Yield (%) | 100 | 77.7 | 78.8 | 19.9 |

The acid- and thermostability of partially purified alpha-amylase preparations from ATCC Nos. 31,195 and 31,199 and Thermamyl alpha-amylase (having 7 units/ml) were determined by incubation for 60 minutes under the following conditions:

(a) *90° C., pH 6.0, $Ca^{++}$ 0 or 1 mM;
(b) *80° C., pH 4.5, $Ca^{++}$ 5 mM; and
(c) **85° C., pH 4.55, $Ca^{++}$ 1 mM or 5 mM, 22.5% soluble starch.

*5 ml of the alpha-amylase preparation was dialyzed in a Visking 8/32 cellulose tube against 0.05 M calcium acetate buffer (pH 4.5–6.0) containing 0–5 mM of calcium acetate for three hours at 4° C., changing the buffer twice. Then 4 ml of the dialyzates were put to small test tubes and incubated at the designated temperature in a water bath. The tubes were rapidly cooled in an ice water bath and the residual alpha-amylase activity was determined.

**0.3 ml of a dialyzed enzyme solution of alpha-amylase, 0.5 ml of 1 M calcium acetate buffer, 0.2 ml of 0.5 M $CaCl_2$, and 3.0 ml of 30% soluble starch slurry were pipeted into a test tube. The mixture was then incubated 85° C. for 30 minutes with continuous stirring. Then test tubes were rapidly cooled in an ice water bath and the residual alpha-amylase activity was determined.

The residual alpha-amylase activities were determined after 5, 10, 20, 30 and 60 minutes of incubation.

The optimum pH and temperature of the ATCC No. 31,195 and ATCC No. 31,199 alpha-amylases and Thermamyl alpha-amylase were determined by the CPC assay conditions described above except that the reaction pH or temperature was changed. The results of the tests are shown in FIGS. 1 and 2. The optimum pH of both ATCC No. 31,195 and ATCC No. 31,199 alpha-amylase was 4.0–5.2 and that of Thermamyl alpha-amylase was 4.5. The Thermamyl alpha-amylase was found to retain a high enzymatic activity over a neutral and alkaline pH range.

The optimum temperatures were 75° C. for ATCC No. 31,199 alpha-amylase, 80° C. for ATCC No. 31,195 alpha-amylase and 85° C. for Thermamyl alpha-amylase. The relationship between enzymatic activity and reaction temperature was very similar for the ATCC No. 31,195 and ATCC No. 31,199 alpha-amylases, but that for Thermamyl alpha-amylase was very different. It was found that the alpha-amylase activity of Thermamyl alpha-amylase was increased by 20–30% when it was incubated at 85° C. and pH 6.0 in the presence of starch and $Ca^{++}$. This fact may explain the difference in the enzymatic activity-reaction temperature relationship between the ATCC No. 31,195 and ATCC No. 31,199 alpha-amylases and Thermamyl alpha-amylase.

FIG. 3 illustrates the inactivation curves of the ATCC No. 31,195 and ATCC No. 31,199 alpha-amylases and Thermamyl alpha-amylases when they were incubated at 80° C. and pH 4.5 in the presence of 5 mM $CaCl_2$. ATCC No. 31,199 alpha-amylase showed the highest thermostability followed by ATCC No. 31,195 alpha-amylase. Thermamyl alpha-amylase was considerably inferior to the ATCC No. 31,195 and ATCC No. 31,199 alpha-amylases in thermostability under these conditions.

FIG. 4 illustrates the inactivation curves of the ATCC No. 31,195 and ATCC No. 31,199 alpha-amylases, Thermamyl alpha-amylase and *Bacillus stearothermophilus* alpha-amylase described by Ogasawara et. al. (*J. Biochem.*, 67, 65, 77, 83 (1970)) when they were incubated at 90° C., and pH 6.0 in the absence of $Ca^{++}$ (the incubation conditions described by Ogasawara et. al. were the same as used in this test).

As it can be seen from FIG. 4, the alpha-amylases of the present invention showed much higher thermostability than either Thermamyl alpha-amylase or the Ogasawara et. al. alpha-amylase (even though the alpha-amylases of the present invention tested also belong to *Bacillus stearothermophilus*).

Figure 5:
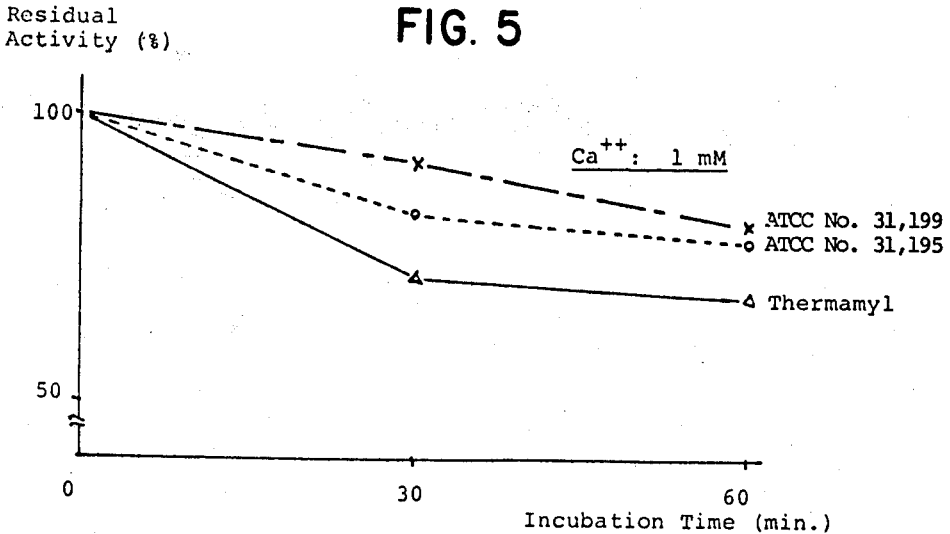
FIG. 5 compares the thermostability of two of the enzymes of the invention with Thermamyl alpha-amylase at 90° C., a pH of 6.0 and in the presence of 1 mM $Ca^{++}$.

FIG. 5 illustrates the inactivation curves of the ATCC No. 31,195 and ATCC No. 31,199 alpha-amylases and Thermamyl alpha-amylase under the same conditions as described above for FIG. 4 (e.g., 90° C. and pH 6.0) except that the medium contained 1 mM Ca++. The alpha-amylases of the present invention still showed higher thermostability than Thermamyl alpha-amylase, but the difference was not as great as in the case of no added Ca++. These facts tend to indicate that the ATCC No. 31,195 and ATCC No. 31,199 alpha-amylase bind Ca++ more firmly than the Thermamyl alpha-amylase, therefore their requirement for Ca++ to stabilize the protein molecule is less than that of Thermamyl alpha-amylase.

Figure 6:
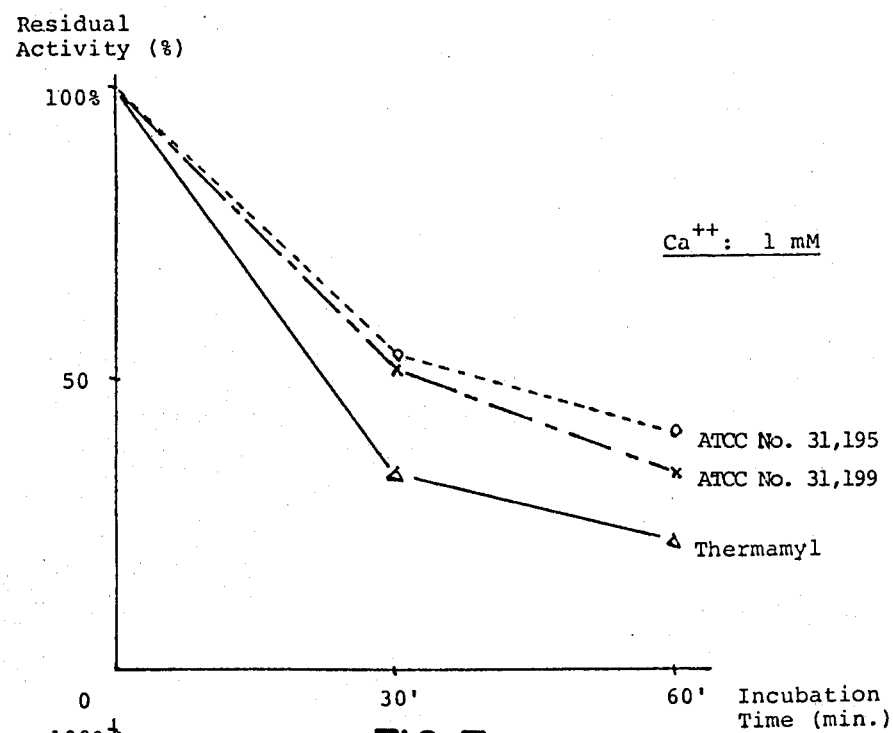
FIG. 6 illustrates the relationship of the thermostability of two of the enzymes of the present invention with Thermamyl at 85° C. and at a pH of 4.55 in the presence of 22.5% starch, d.s.
Figure 7:
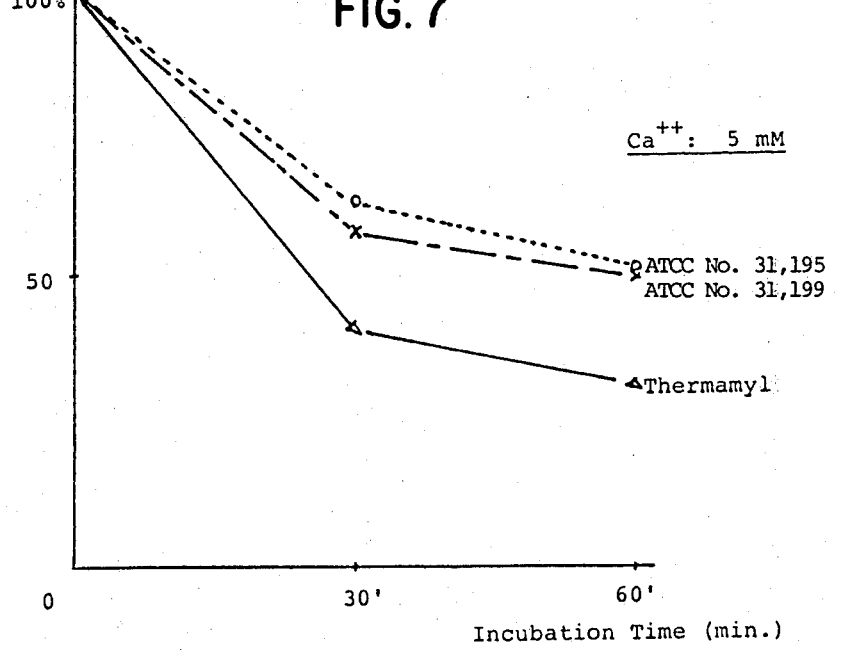
FIG. 7 illustrates the relationship of the thermostability of two of the enzymes of the present invention with Thermamyl alpha-amylase at 85° C., a pH of 4.55 in the presence of 22.5% starch and 5 mM $Ca^{++}$.

FIGS. 6 and 7 illustrate the inactivation curves of the ATCC No. 31,195 and ATCC No. 31,199 alpha-amylases and the Thermamyl alpha-amylase when they were incubated at 85° C. and at a pH of 4.55 in the presence of soluble starch (22.5%, d.s.) and Ca++ (1 mM Ca++ as illustrated in FIG. 6 and 5 mM Ca++ as illustrated in FIG. 7). The ATCC No. 31,195 and ATCC No. 31,199 alpha-amylases showed higher thermostability than Thermamyl alpha-amylase under the conditions of both FIGS. 6 and 7. Since the conditions of the above tests illustrated in FIGS. 6 and 7 are similar to many industrial liquefaction conditions, it is to be expected that the alpha-amylases of the present invention would demonstrate higher thermostability at acidic pH values in the industrial liquefaction and conversion of starch.

Figure 8:
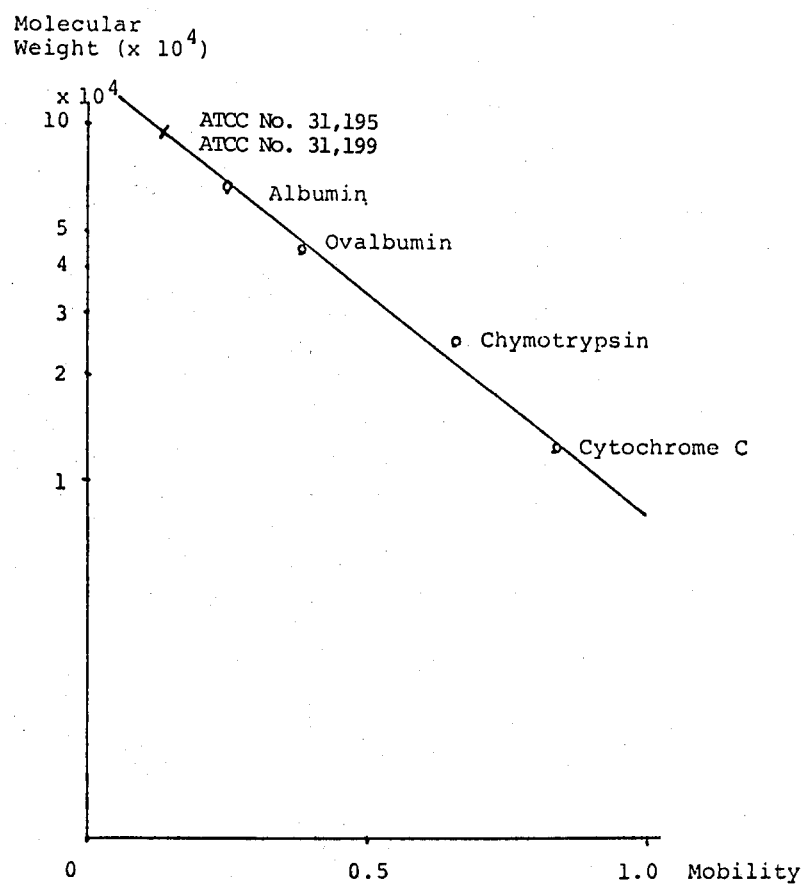
FIG. 8 illustrates graphically the determination of the molecular weight of two enzymes of the invention by SDS disc electrophoresis.

The molecular weights of both ATCC No. 31,195 and ATCC No. 31,199 alpha-amylases were determined to be 96,000 as measured by the method of Weber and Osborn, *J. Biol. Chem.*, 244, 4406 (1969) by the use of SDS disc electrophoresis. The marker proteins were albumin (M. W. 67,000), ovalbumin (M. W. 45,000), chymotrypsin (M. W. 25,000) and cytochrome C (M. W. 12,500). The position of the alpha-amylases of the present invention on the polyacrylamide gel was determined by putting the gel on an Amylose-Azure agar plate and incubating it at 37° C. The results of this test are illustrated in FIG. 8.

The value of 96,000 for the molecular weight of the alpha-amylases of the present invention is much larger than those for the *Bacillus stearothermophilus* alpha-amylases reported by Ogasawara et. al., *J. Biochem.*, 67, 65, 77, 83 (1970) (M. W. reported as 48,000) and by Manning et. al. *J. Biol. Chem.*, 236, 2952, 2958, 2962 (1961) (M. W. reported as 15,600).

The five isolated strains were tested for protease activity since the presence of protease or proteolytic enzyme in alpha-amylase enzymes tends to react with various proteinaceous materials present in many starchy materials to produce water soluble protein hydrolysates such as amino acids. For this reason, the presence of the protease enzyme contaminant in alpha-amylase enzymes is detrimental to the efficient hydrolysis of starchy materials. The protease activities in the alpha-amylase enzymes produced from the five isolated strains were determined from acetone precipitates of culture filtrates at the stage of maximum alpha-amylase production using a modified Anson-Hagiwara method. The results obtained were compared with enzyme preparations of Thermamyl alpha-amylase and a CPC bacterial alpha-amylase. As shown below, Thermamyl and the culture filtrates of isolated thermophilic ray fungi contained large quantities of protease. On the other hand, the thermostable alpha-amylase-producing strains of the present invention produced no significant amount of protease.

PROTEASE ACTIVITY OF ALPHA-AMYLASE

| Enzyme | Protease/Alpha-Amylase Ratio |
|---|---|
| ATCC No. 31,195 | 0.06 |
| ATCC No. 31,196 | 0.17 |
| ATCC No. 31,197 | 2.35 |
| ATCC No. 31,198 | 0.08 |
| ATCC No. 31,199 | 0.06 |
| CPC-BLA | 6.2 |
| Thermamyl 60 | 36.5 |
| B-172[1] | 109.0 |

[1]Thermophilic ray fungi isolated at 55° C. at a pH of 7.0.

As it can be seen from the above results the alpha-amylases of the present invention do not contain any significant amounts of protease activity, i.e., a protease-/alpha-amylase ratio of less than 3 and generally less than 1. This is a significant advantage when using the enzyme to hydrolyze starchy materials.

EXAMPLE 3

The strain of the present invention corresponding to ATCC No. 31,199 (B-968) was mutated to develop strains having higher α-amylase activity. The various media that were utilized are identified in Table 9.

Sixty-eight colonies of B-968 were cultured in the seed medium at 55° C. for 16 hours with reciprocal shaking at 130 rpm. The cells were washed and suspended in sterile water. Ethyleneimine was then added so that final concentration was one microliter per milliliter. Forty-seven percent of the colonies yielded 30–40 CPC alpha-amylase units per milliliter of the culture filtrate.

One strain, identified as M-1041, from the foregoing procedure, was selected for further treatment. It was cultured in the seed medium in accordance with the foregoing procedure followed by washing and suspension in sterile water. It was then irradrated with ultra violet rays for 20 seconds with magnetic stirring in a petri dish placed 28 centimeters under an ultra violet lamp. Three percent of the colonies collected had activities of 80 to 100 CPC alpha-amylase units per milliliter of the culture filtrate.

A strain, identified as M-1327, from the colonies having activities of 80 to 100 CPC alpha-amylase units per milliliter was selected for further treatment. It was cultured for 5 hours at 55° C. in the main medium. The cells were washed with sterile water and suspended and stirred for 30 minutes in 5 milliliters of a phosphate buffer containing 100 micrograms per milliliter of N-methyl-N'-nitro-N-nitroso-guanidine at a pH of 6.0 and room temperature. A mutant strain from this procedure was identified as M-1717.

TABLE 9

| | Composition of media (%, w/v) | | | |
|---|---|---|---|---|
| | Slant | Plate | Seed | Main |
| Soluble starch | 1.0 | 3.0 | — | — |
| Corn Starch | — | — | — | 6.0 |
| Amylose azure | — | 0.1 | — | — |
| CSL* | — | — | — | 1.0 |
| Bacto-tryptone | 0.5 | 0.5 | — | — |
| Yeast ext. | 0.5 | 0.5 | 1.0 | 0.5 |
| Pharmamedia | — | — | — | 4.0 |
| $CaCl_2 \cdot 2H_2O$ | 0.05 | 0.05 | 0.05 | 0.1 |
| $MgSO_4 \cdot 7H_2O$ | — | 0.05 | 0.05 | 0.05 |
| $MnCl_2 \cdot 4H_2O$ | 0.05 | 0.0001 | 0.0001 | 0.001 |
| $KH_2PO_4$ | 0.1 | 0.1 | 0.1 | — |
| NaCl | — | — | — | 0.05 |

TABLE 9-continued

| | Composition of media (%, w/v) | | | |
|---|---|---|---|---|
| | Slant | Plate | Seed | Main |
| Agar | 2.0 | 2.0 | — | — |
| pH | 6.0 | 6.0 | 6.0 | 6.25 |

M-1717 was subdivided into three types, A, B and C. Type B showed the most stable production of the enzyme and the best alpha-amylase activity. (190–290 CPC alpha-amylase units per milliliter of the culture filtrate). This strain, M-1717 B, was cultured in the main medium under the same conditions as M-1327, followed by washing and suspending in the same manner. A mutant strain, identified as N-21, had an activity of 330 to 490 CPC alpha-amylase units per milliliter of the culture filtrate.

For purposes of this experiment, positive mutants were selected by diluting the mutagen-treated cells, pouring the diluted cells on the plate medium and culturing overnight at 70° C. Clear zones around the colonies were formed by hydrolysis of the amylose azure in the plate medium.

Slants were made on the slant medium from colonies having the largest clear zones and cultured overnight at 70° C. The highest yielding strains were selected, purified and retested and subsequently given new mutagenic treatment.

EXAMPLE 4

Further experimental production of α-amylase was conducted as follows:

A. 10 l Fermentor
   The first stage medium listed in Table 10 was used for the seed development. N-21 was transferred to a 500 ml-Sakaguchi flask containing 50 ml of the 1st-stage medium, and was grown for 24 hrs. at 56° C. on a reciprocal shaker (130 cpm).

B. 2,000 l Fermentor
   200 ml of the first stage seed culture in the flask was transferred to the 30 l-fermentor containing 20 l of the second stage seed medium.

This was grown for 24 hrs. under the conditions described in Table 11.

The media were sterilized as follows:
A. Flask Medium
   120° C., 15 min. (autoclaving)
B. 10 l- and 30 l-fermentors
   100° C., 30 min. and then 120° C., 15 min. (using steam jacket)
C. 2,000 l-fermentor
   Medium ingredients were added to hot water (65° C.), and then the temperature was increased to 110° C. using a jacket and a heat-exchanging coil installed in the fermentor. The holding time was 15 min. at 110° C.

TABLE 10

| | Medium Compositions | | |
|---|---|---|---|
| | Seed Culture | | Main Culture |
| | 1st stage | 2nd stage | Fermentor |
| Corn Starch | 3.0 | 7.8 | 7.8 |
| Yeast Ext. | 0.25 | 0.65 | 0.65 |
| Pharmamedia | 2.0 | 5.2 | 5.2 |
| CSL | 0.5 | 1.3 | 1.3 |
| HVP* | — | — | 2.0 |
| CaCl$_2$ . 2H$_2$O | 0.05 | 0.13 | 0.13 |
| MgSO$_4$ . 7H$_2$O | 0.025 | 0.065 | 0.065 |
| MnCl$_2$ . 4H$_2$O | 0.0005 | 0.0013 | 0.0013 |
| NaCl | 0.025 | 0.065 | — |
| Thermamyl | 0.015 | 0.04 | 0.04 |
| Anti-foam** | — | 0.1 | 0.1 |
| pH | 6.3 | 6.3 | 6.3 |

*50% solution of acid-hydrolyzed soybean protein containing 20% NaCl. (Ajinomoto Co., Ltd.)
**Silicone SH5504 (Toray Silicone Co., Ltd.)

TABLE 11

| Operating Procedures for Stirred Fermentation | | | |
|---|---|---|---|
| Total Volume (l) | 10 | 30 | 2,000 |
| Operating Volume (l) | 5 | 20 | 1,200 |
| Inoculum Volume (l) | 0.05 | 0.2 | 20 |
| Agitation (rpm) | 600 | 450 | 380 |
| Air Flow (lpm) | 5 | 10 | 1,000 |
| Temperature (°C.) | 56 | 56 | 56 |
| Culturing Period (hrs) | 24 | 24 | 28 |
| Impeller Type | Turbine | Turbine | Turbine |
| Number of Blades | 8 | 6 | 6 |
| Number of Baffles | 3 | 3 | 4 |

Yields were as follows:
A. 10 l-fermentor: 500 CPC alpha-amylase units per milliliter
B. 2,000 l-fermentor: 230 CPC alpha-amylase units per milliliter

EXAMPLE 5

The following example illustrates the use of the alpha-amylase enzymes of the present invention in liquefying starch in the manufacture of high D. E. starch hydrolysates.

Thirty grams of potato starch were suspended in 70 ml of water, 75 mg of calcium chloride dihydrate was added and the pH was adjusted to 4.5. To this slurry there was added 50 CPC units of the refined, powdered enzyme obtained in Example 2 to liquefy the starch at 85° C. for 30 minutes. The D. E. of the liquefied solution was about 21 and the pH was 4.3. When the temperature had decreased to 60° C., a glucoamylase enzyme derived from *Aspergillus niger* was added and the solution was saccharified and converted at 60° C. for 48 hours. The D. E. of the saccharified and converted solution was 97.5 and its dextrose content was 96.0%.

As shown in the preceding example (Example 3), the alpha-amylase enzyme of the present invention hydrolyze and liquefy starch. They can be used to convert soluble starch, amylose, amylopectin, glycogen, etc., to abruptly reduce the viscosity of these substrates. When the enzymes of the present invention react with soluble starch at pH 4.5 and 60° C., the starch-iodide reaction disappears at a hydrolysis rate (D. E.) of about 15 and the ultimate rate is a D. E. of 32 to 36. The sugars of the hydrolyzed product were analyzed as maltose, maltotriose, maltotetrose and other maltooligosaccharides together with a small quantity of glucose. The mutarotation of the reducing sugar product has been found to be negative. Accordingly, the enzymes of this invention are alpha-amylase enzymes of the liquefying type and freely hydrolyze the alpha- 1,4 bonds of starch.

Figure 9:
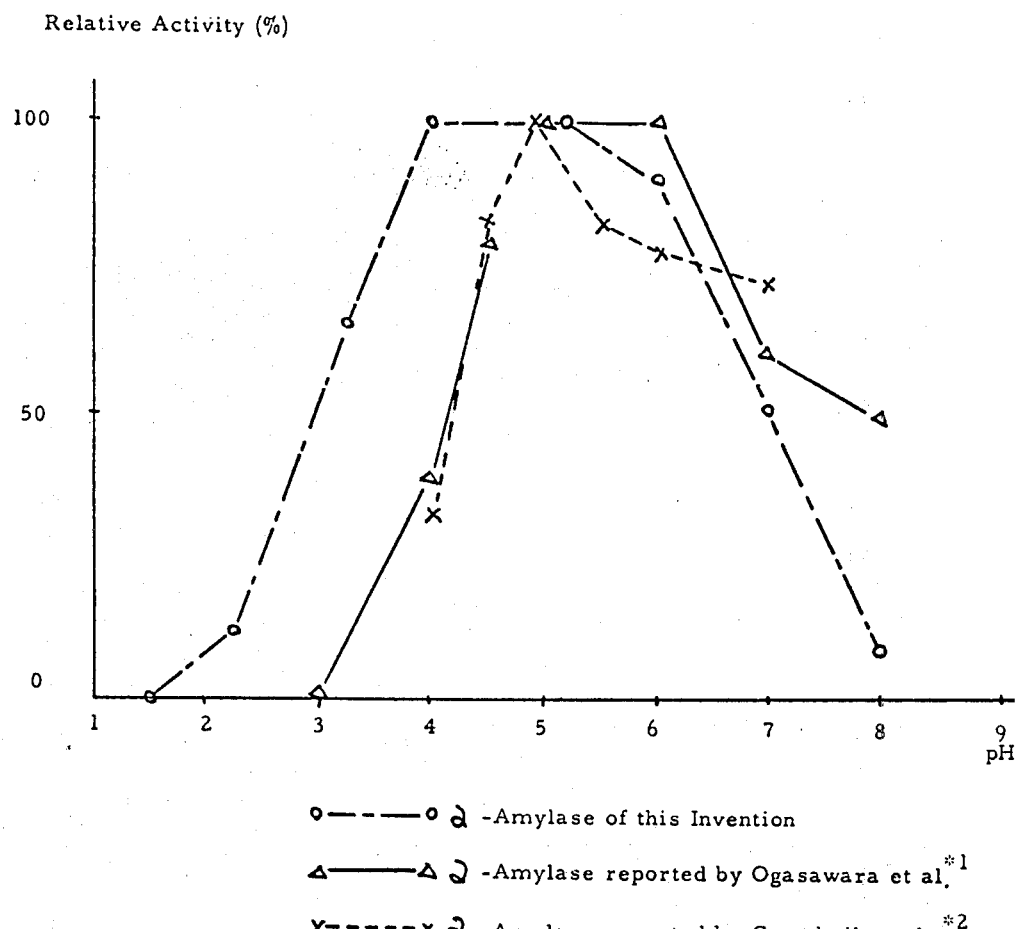
FIG. 9 illustrates the relationship between pH and enzyme activity as to one of the enzymes of the invention with prior art alpha-amylases derived from Bacillus stearothermophilus microorganisms.

The relationship between liquefaction using the enzyme of the present invention (relative value) and the operational pH is shown in FIG. 9 and it is contrasted with the known alpha-amylase enzymes derived from

*Bacillus stearothermophilus.* As shown in FIG. 9, the optimal pH for the enzymes of the present invention is pH 4.2 to pH 5.2. The preferred enzymes of the present invention do not lose their activity even if they are left for 24 hours at room temperature at pH's in the range from 3 to 11.

Figure 10:
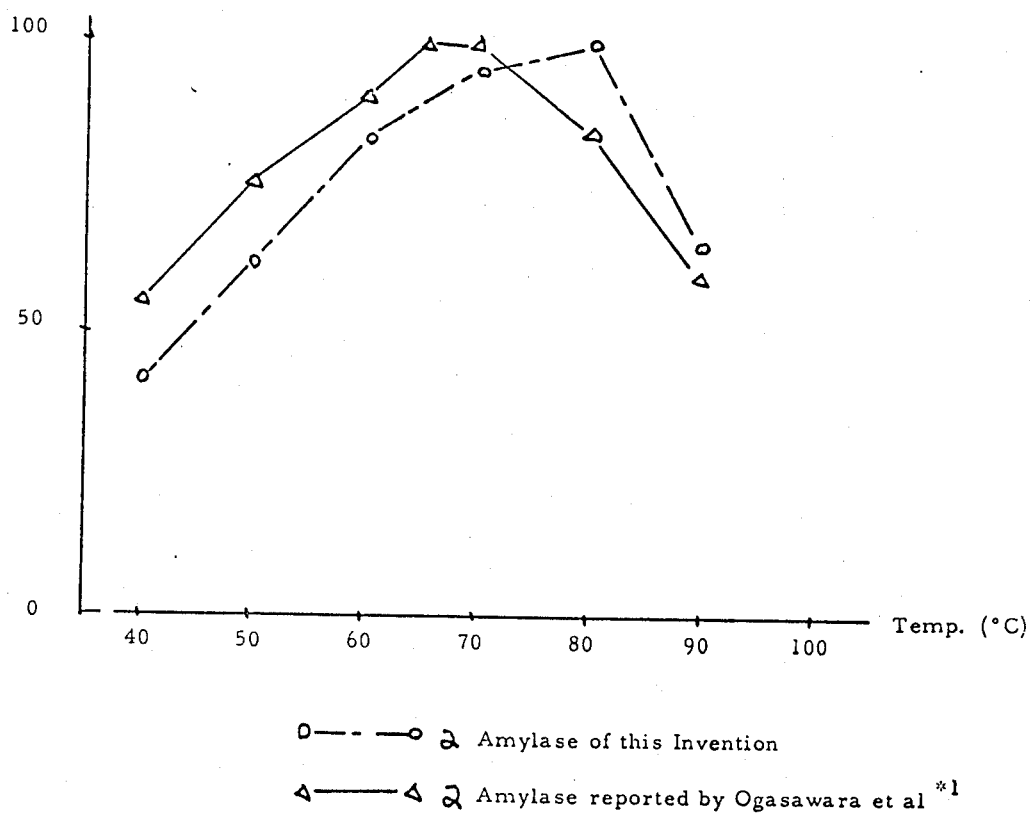
FIG. 10 illustrates the relationship between temperature of an enzyme of the present invention with a prior art alpha-amylase derived from Bacillus stearothermophilus.

The relationship between liquefaction by the enzymes of the present invention (relative value) and the operational temperature is shown in FIG. 10 and contrasted with that of the alpha-amylase derived from *Bacillus stearothermophilus* described by Ogasawara et. al. As shown in FIG. 10, the preferred operational temperature for the enzymes of the present invention is about 80° C.

As apparent from the foregoing, the alpha-amylase enzymes of the present invention can be used in the liquefaction and conversion of starch in the starch saccharification industry, desizing process in the textile industry and as additives in detergent formulations similarly to the conventional uses for bacterial alpha-amylase enzymes.

The alpha-amylase enzymes of the present invention are particularly suited in the liquefaction and conversion of starch in the production of malto-dextrins, subsequent production of dextrose using glucoamylase since isomerization of the end group of the molecules can be avoided because the enzyme can be efficiently used at an acidic pH (i.e. a pH of 4.5-5.0), thereby increasing the dextrose yield. The use of these novel enzymes also reduces the ion exchange load in the refining process because no pH adjustment is required prior to saccharification and conversion with the glucoamylase enzyme.

In one preferred manner of using the alpha-amylase enzymes of the present invention, the enzyme is used to convert starch to a starch hydrolysate wherein the residual unconverted starch remains in its granular form. These processes are described and claimed in U.S. Pat. Nos. 3,922,196; 3,922,197; 3,922,198; 3,922,199; 3,922,200 and 3,922,201, all issued Nov. 25, 1975, the entire contents of which are incorporated herein by reference. In these granular starch procedures, at least the initial solubilization of the starchy material is carried out at relatively low temperatures, i.e., below the initial gelatinization temperature of the starch up to the actual initial gelatinization temperature of the starch. In a preferred manner of carrying out these processes, the glucoamylase enzyme is used concurrently with the alpha-amylase enzyme in the initial solubilization stage. The enzymes of the present invention are particularly suited for this process because their optimal pH range is compatible with glucoamylase.

In another preferred manner of using the alpha-amylase enzymes of the present invention one can use the processes described in U.S. Pat. No. 3,853,706, issued Dec. 10, 1974 and U.S. Pat. No. 3,849,194 issued Nov. 19, 1974, the disclosures of which are incorporated herein by reference.

In still another preferred manner of using the alpha-amylase enzymes of the present invention one can use the process described in U.S. Pat. No. 3,912,590, issued Oct. 14, 1975 to Slott et. al. and assigned to Novo Industri A/S, the disclosure of which is incorporated herein by reference. By use of the alpha-amylase enzymes of the present invention with the Slott et. al. process, a slurry of starch, such as corn starch having at least 25% by weight starch material is treated with the alpha-amylase enzyme at a temperature in the range from about 100° C. to about 115° C., preferably from 105° C. to about 110° C. for 1 to 60 minutes, and preferably 5-10 minutes to liquefy the starch and thereafter reduce the temperature to 80°-100° C. and preferably 90° C. to 100° C. when the viscosity of the thinned solution is less than 300 c.p.s. measured at 95° C. The unique advantage of applying this temperature profile procedure with the alpha-amylase enzymes of the present invention is that a lower pH can be used so that little or no pH adjustment is needed in a subsequent saccharification procedure with glucoamylase.

The most preferred use of the alpha-amylase enzymes of the present invention for converting starch include subjecting a starch slurry to the action of the enzyme at a pH in the range from about 3.5 to about 6.5, preferably from about 4 to about 5, at a temperature ranging from about 50° C. to about 100° C., and preferably 60° C. to about 95° C. to liquefy the starch. In the case of the granular starch hydrolysis processes described above the temperature will range from the normal initial gelatinization temperature to the actual initial gelatinization temperature of the starch, i.e. about 60° C. for corn starch. In the case of a direct liquefation procedure, the starch slurry containing the enzyme is preferably heated (e.g. by a jet heater) to a temperature ranging from about 85° C. to about 95° C. and more preferably from about 90° C. to about 92° C. to liquefy the starch. Following the initial solubilization (as in the granular starch hydrolysis) or liquefaction, the slurry is preferably subjected to a "heat-shock" treatment at a temperature above 100° C. and preferably ranging from about 110° C. to about 150° C. to liquefy any residual starch granules. Thereafter, the liquefied starch slurry is cooled and preferably treated with additional alpha-amylase, alone or in combination with other enzymes such as glucoamylase, beta-amylase, pulluanase, glucose isomerase, sequentially or in combination. If alpha-amylase is used alone in the second enzyme stage the temperature will preferably range from about 80° C. to about 90° C. and most preferably about 85° C., the optimum temperature for the enzymes of the present invention. If other enzymes are present such as glucoamylase and/or glucose isomerase, the temperature will be somewhat lower, i.e., 55°-75° C. and preferably about 60° C.

CONCLUSION

Figure 11:
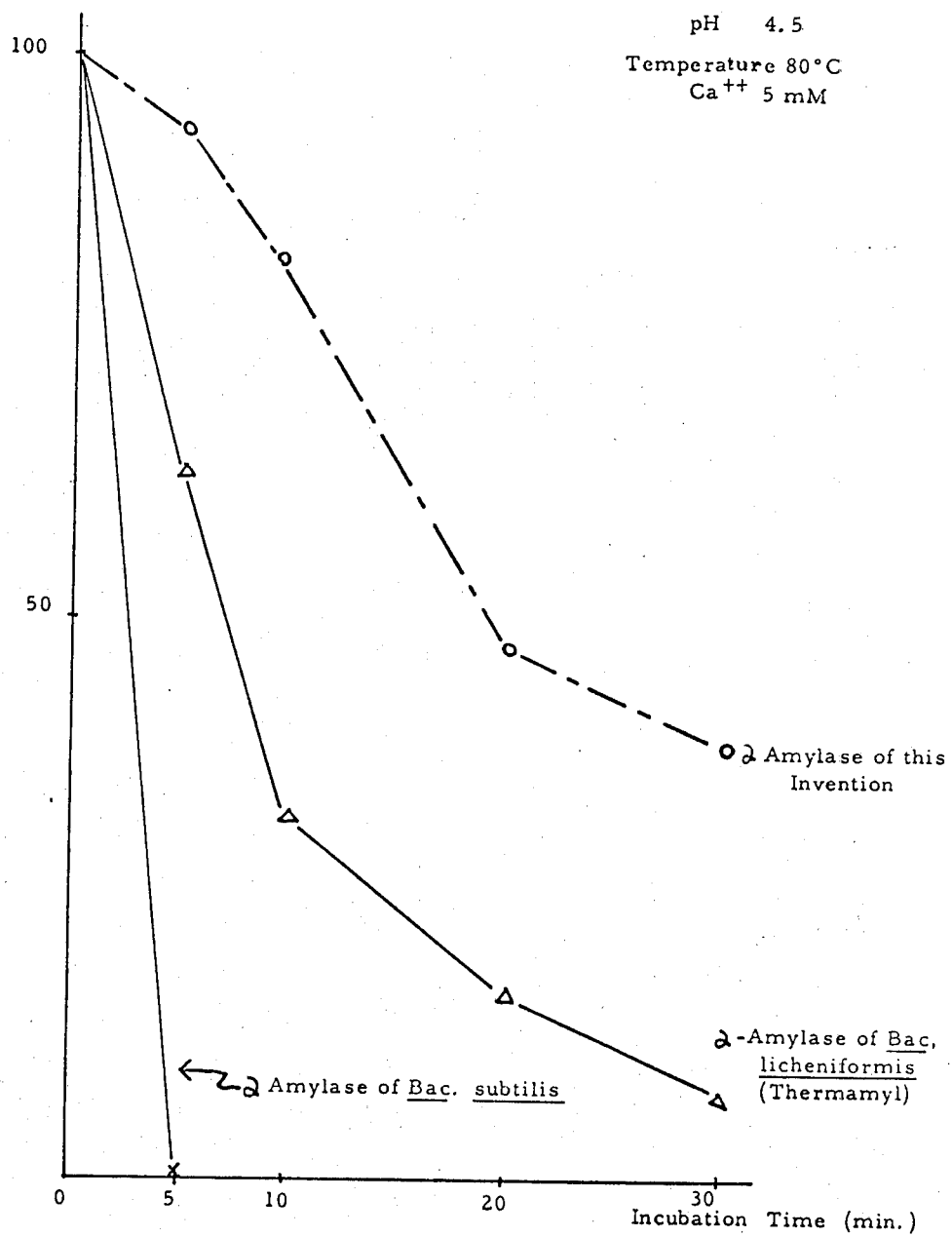
FIG. 11 illustrates the deactivation curves of an enzyme of the present invention with prior art alpha-amylases derived from Bacillus subtilis and Bacillus licheniformis when treated at 80° C. and pH 4.5 in the presence of 5 mM calcium ion.
Figure 12:
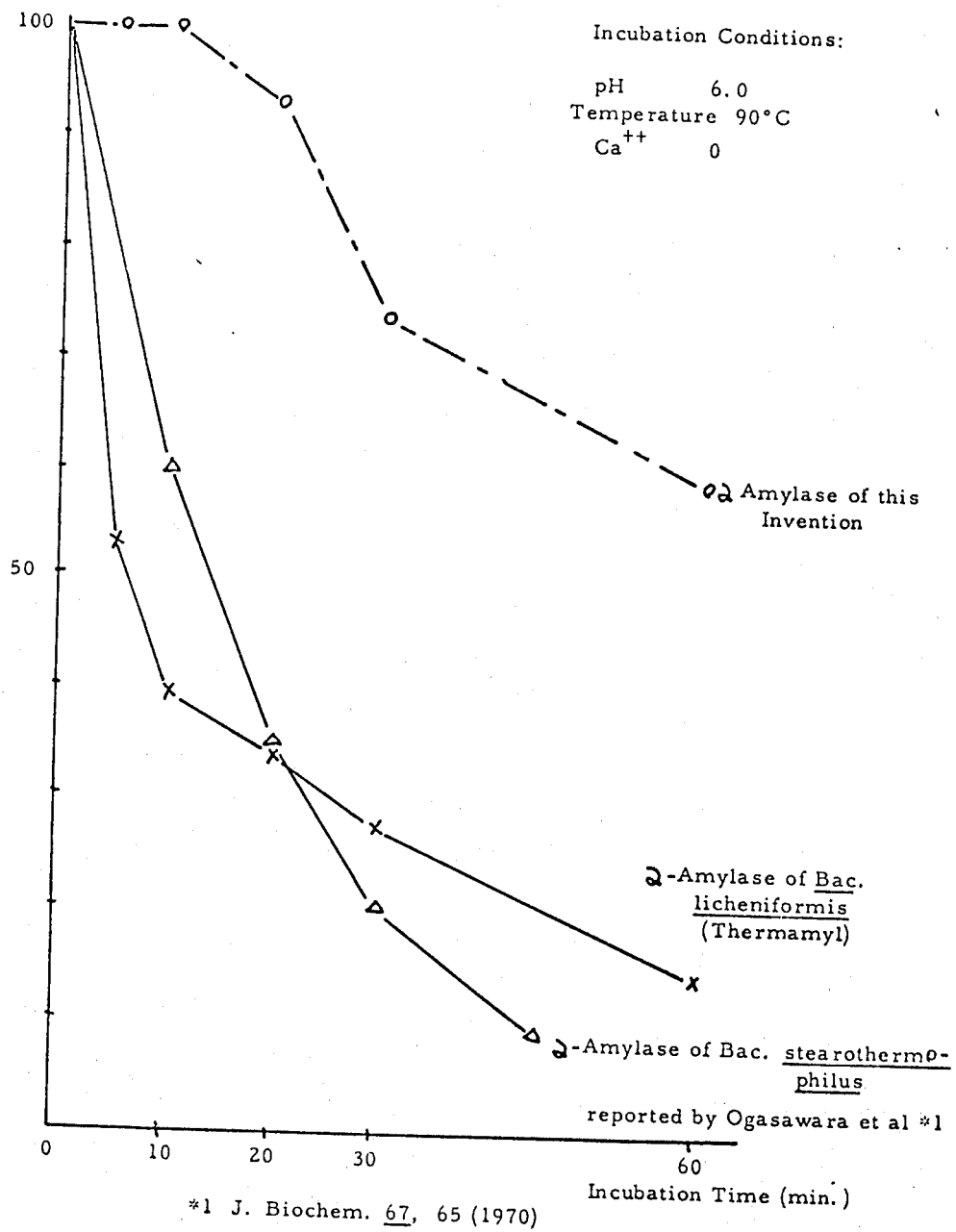
FIG. 12 illustrates the deactivation curves of an enzyme of the present invention with prior art alpha-amylases derived from Bacillus licheniformis and Bacillus stearothermophilus when treated at 90° C. and at a pH of 6.0 without calcium ion.

The alpha-amylase enzymes of the present invention can be clearly differentiated from the prior art alpha-amylases obtained from animals, plants, yeasts, imperfect fungi, and molds inasmuch as these prior art enzymes have such a low heat-stability that they completely lose their activity upon 5 minutes treatment at 70° C. and pH 6.0. By comparing the heat-stability of the alpha-amylases of the present invention as shown in FIG. 12 (the data for preparing FIG. 12 is substantially the same as that used for FIG. 4) it is clear that the alpha-amylase enzymes of the present invention are far superior as to acid- and heat-stability compared to the prior art alpha-amylase enzymes compared. It is also apparent from FIG. 12 that the alpha-amylase enzymes of the present invention are characterized as capable of retaining at least about 70% and preferably at least about 90% of their initial activity when held at 90° C. and at a pH of 6.0 for 10 minutes in the absence of added calcium ion and capable of retaining at least about 50% of their initial alpha-amylase activity when held at 90° C. at a pH of 6.0 for 60 minutes in the absence of added calcium ion. As seen from FIG. 11, it is apparent that the alpha-amylase enzymes of the present invention are further characterized as capable of retaining at least about 50% of their initial alpha-amylase activity at a temperature of 80° C. and at a pH of 4.5 in the presence of 5 mM of calcium ion for 10 minutes.

Table 12 shows the relationship between the alpha-amylase enzymes of the present invention and the alpha-amylase enzymes *Bacillus subtilis* and *Bacillus licheniformis* which are employed industrially, and those of *Bacillus stearothermophilus* described in the literature. They are compared with respect to optimal operational pH, proper operational temperature, and molecular weight. FIGS. 11 and 12 contrast their properties of heat- and acid-stabilities.

TABLE 12

| Enzymes Tested | Optimal Operational pH | Proper Operational Temperature | Molecular Weight |
|---|---|---|---|
| Alpha-amylase enzymes of this invention | 4.0–5.2 | 80° C. | 96,000 |
| Alpha-amylase of *B. Subtilis*[1] | 4.5–6.5 | 45–60° C. | 49,000[5] |
| Alpha-amylase of *B. licheniformis*[2] | 5.0–9.0 | 76–78° C. | 22,500[5] |
| Alpha-amylase of *B. stearothermophilus* | | | |
| (a) Ogasawara et. al.[1] | 5.0–6.0 | 65–70° C. | 48,000 |
| (b) Campbell et. al.[3] | 4.8 | 55–70°C. | 15,600[4] |

[1]Ogasawara et. al., J. Biochem., 67, 65 (1970).
[2]Shigemasa Saito, ABB, 155, 290 (1973).
[3]Campbell et. al., J. Biol. Chem., 236, 2952 (1961).
[4]Campbell et. al., J. Biol. Chem., 236, 2958 (1961).
[5]British Patent Specification No. 1,296,839 reports the molecular weight of alpha-amylase from *B. licheniformis* to be 10,000–20,000 and *B. subtilis* 96,000.

When the alpha-amylase enzymes of the present invention are compared with the alpha-amylase enzymes from *Bacillus subtilis*, the two are seen to be remarkably different, as is clear from FIGS. 9 and 11, in their optimal operational pH, proper operational temperature, molecular weight and heat- and acid-stability. This indicates that this enzyme is quite different from the alpha-amylase of *Bacillus subtilis*.

When the alpha-amylase enzymes of the present invention and the alpha-amylase enzymes from *Bacillus licheniformis* are compared, they are remarkably different in their optimal operational pH, molecular weight and heat- and acid-stability as is shown in Table 12, and FIGS. 11 and 12.

As it will be apparent to those skilled in the art, the strains used to produce the novel alpha-amylase enzymes of the present invention may be subjected to mutagenic agents known using known techniques, such as ultra-violet light, chemical treatment and the like. Accordingly, the present invention contemplates alpha-amylase enzymes produced from the strains of ATCC Nos. 31,195, 31,196, 31,197, 31,198, 31,199, variants and mutants of these strains, and submutants of said variants and mutants.

Like some of the other known alpha-amylase enzymes, the enzymes of the present invention are inhibited by mercury and EDTA, but are stabilized by calcium.

It will be understood by those skilled in the art that various modifications of the present invention as described in the foregoing examples may be employed without departing from the scope of the invention. Many variations and modifications thereof will be apparent to those skilled in the art and can be made without departing from the spirit and scope of the invention herein described.

We claim:

1. A heat and acid-stable alpha-amylase enzyme derived from a *Bacillus stearothermophilus* microorganism and having a pH optimum between 4.0 and 5.2 characterized as (1) capable of retaining at least about 70% of its initial alpha-amylase activity when held at 90° C. and at a pH of 6.0 for 10 minutes in the absence of added calcium ion; (2) capable of retaining at least about 50% of its initial alpha-amylase activity when held at 90° C. at a pH of 6.0 for 60 minutes in the absence of added calcium ion; and (3) capable of retaining at least about 50% of its initial alpha-amylase activity when held at 80° C. and at a pH of 4.5 for 10 minutes in the presence of 5 mM of calcium ion.

2. The alpha-amylase enzyme of claim 1, wherein said enzyme is capable of retaining at least about 50% of its initial alpha-amylase activity at a temperature of 85° C. and at a pH of 4.55 for 30 minutes in the presence of 5 mM of calcium ion and 22.5%, by weight, starch, d.s.

3. A process for converting starch to a starch hydrolysate comprising:
   (a) treating an aqueous slurry of starch with the alpha-amylase enzyme of claim 1 at a pH of 3.5 to 6.5 to liquefy and convert the starch; and
   (b) obtaining a starch hydrolysate from the conversion of step (a).

4. The process of claim 3, wherein the treatment in step (a) is conducted at a temperature in the range from about 50° C. to about 100° C. at a pH of 4 to about 5.

5. The process of claim 3, wherein the starch hydrolysate is treated with a glucoamylase enzyme.

6. The process of claim 3, wherein the starch hydrolysate is heated to a temperature above 100° C. and thereafter cooled and treated with additional alpha-amylase.

7. The process of claim 3, wherein the starch hydrolysate is treated with a glucose isomerase enzyme.

8. A heat and acid-stable alpha-amylase enzyme characterized as having a pH optimum between 4.0 and 5.2 and as being derived from a strain of *Bacillus stearothermophilus* which is a member selected from the group consisting of ATCC Nos. 31,195 and 31,999, variants and mutuants thereof and sub-mutants of said mutants.

9. The alpha-amylase enzyme of claim 6, wherein the *Bacillus stearothermophilus* strain is a mutant of a mutant strain of ATCC No. 31,199.

10. A process for converting starch to a starch hydrolysate comprising:
    (a) treating an aqueous slurry of starch with the alpha-amylase enzyme of claim 9 at a pH of 3.5 to 6.5 to liquefy and convert the starch; and
    (b) obtaining a starch hydrolysate from the conversion of step (a).

11. The process of claim 10, wherein the treatment in step (a) is conducted at a temperature in the range from about 50° C. to about 100° C. at a pH of 4 to about 5.

12. The process of claim 10, wherein the starch hydrolysate is treated with a glucoamylase enzyme.

13. The process of claim 10, wherein the starch hydrolysate is heated to a temperature above 100° C. and thereafter cooled and treated with additional alpha-amylase.

14. The process of claim 10, wherein the starch hydrolysate is treated with a glucose isomerase enzyme.

15. A process for the preparation of a heat and acid stable alpha-amylase enzyme, comprising culturing a microorganism strain selected from the group consisting of *Bacillus stearothermophilus* ATCC Nos. 31,195, 31,196, 31,197, 31,198, 31,199, variants and mutants thereof and sub-mutants of said mutants in a culture medium and recovering the enzyme produced.

16. The process of claim 15, wherein the culture medium contains assimilable carbon and nitrogen sources.

17. The process of claim 15, wherein the cultivation is conducted at a pH in the range from 5 to 9 at a temperature of 50° to about 70° C. for 1 to 5 days.

18. The process of claim 15 wherein the microorganism strain is a mutant of a mutant strain of *Bacillus stearothermophilus* ATCC No. 31,199.

* * * * *

UNITED STATES PATENT AND TRADEMARK OFFICE
CERTIFICATE OF CORRECTION

PATENT NO. : 4,284,722

DATED : August 18, 1981

INVENTOR(S) : Masaki Tamuri, Mitsuo Kanno and Yoshiko Ishii

It is certified that error appears in the above-identified patent and that said Letters Patent are hereby corrected as shown below:

Column 1, line 37, "can" should read --may--.
Column 2, line 9, "mophilis" should read --mophilus--.
Column 8, lines 23 and 24, "plates-treaking" should read --plate-streaking--.
Column 9, line 50, "hyrdoxylapatite" should read --hydroxylapatite--.
Column 10, line 28, after "cellulose" insert --and--.
Column 14, line 23, "amylase" should read --amylases--.
Column 14, line 44, "amylases" should read --amylase--.
Column 15, line 8, "amylase" should read --amylases--.
Column 16, line 39, "irradrated" should read --irradiated--.
Column 17, line 7, --*corn steep liquor-- should be inserted at end of Table 9.
Column 20, line 22, "liquefation" should read --liquefaction--.
Column 20, line 35, "pulluanese" should read --pullulanese--.
Column 22, line 43, "mutuants" should read --mutants--.

UNITED STATES PATENT AND TRADEMARK OFFICE
CERTIFICATE OF CORRECTION

PATENT NO. : 4,284,722  Page 2 of 2
DATED : August 18, 1981
INVENTOR(S) : Masaki Tamuri, Mitsuo Kanno and Yoshiko Ishii It is certified that error appears in the above-identified patent and that said Letters Patent are hereby corrected as shown below:

In the Drawings

Figure 1, in the upper left hand corner delete "Residual" and insert --Relative--.
Figure 3, in the legend at the top of the figure delete "pH 4.55" and insert --pH 4.5--.
Figure 7, in the upper left hand corner insert --Residual Activity (%)-- to define the units for the vertical axis.
Figures 11 and 12, in the upper left hand corners delete "Relative" and insert --Residual--.

Signed and Sealed this

Second Day of November 1982

[SEAL]

Attest:

Attesting Officer

GERALD J. MOSSINGHOFF

Commissioner of Patents and Trademarks